(12) United States Patent
Magno et al.

(10) Patent No.: US 11,723,523 B2
(45) Date of Patent: Aug. 15, 2023

(54) ONE-PIECE ELEVATOR FOR A DUODENOSCOPE

(71) Applicant: GYRUS ACMI, INC., Southborough, MA (US)

(72) Inventors: Joey Magno, Dudley, MA (US); Kurt G. Shelton, Bedford, MA (US); Thomas J. Holman, Princeton, MN (US); Michael Sansoucy, Wrentham, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 141 days.

(21) Appl. No.: 17/126,768

(22) Filed: Dec. 18, 2020

(65) Prior Publication Data

US 2021/0204800 A1 Jul. 8, 2021

Related U.S. Application Data

(60) Provisional application No. 63/024,674, filed on May 14, 2020, provisional application No. 63/024,682, (Continued)

(51) Int. Cl.
*A61B 1/018* (2006.01)
*A61B 1/00* (2006.01)
(Continued)

(52) U.S. Cl.
CPC ............ *A61B 1/018* (2013.01); *A61B 1/0011* (2013.01); *A61B 1/00016* (2013.01);
(Continued)

(58) Field of Classification Search
CPC . A61B 1/00016; A61B 1/018; A61B 1/00087; A61B 1/00096; A61B 1/00098;
(Continued)

(56) References Cited

U.S. PATENT DOCUMENTS 5,460,168 A * 10/1995 Masubuchi ........ A61B 1/00098
600/107
5,489,256 A 2/1996 Adair
(Continued)

FOREIGN PATENT DOCUMENTS

CN 114929083 8/2022
EP 0066120 A2 12/1982
(Continued)

OTHER PUBLICATIONS

"International Application Serial No. PCT/US2020/065965, International Search Report dated Apr. 29, 2021", 6 pgs.
(Continued)

*Primary Examiner* — John P Leubecker
*Assistant Examiner* — Li-Ting Song
(74) *Attorney, Agent, or Firm* — Schwegman Lundberg & Woessner, P.A

(57) ABSTRACT

An elevator for an endoscope comprises a first end secured to the endoscope, a second end movable by an actuator, a flexible portion positioned between the first and second ends that is rotatable when the second end is moved by the actuator, and a guide portion extending between the flexible portion and the second end to receive an endotherapy instrument extending from the endoscope, the guide portion comprising a chute to guide the endotherapy instrument leaving the endoscope. A method of forming an elevator comprises forming from a planar sheet of material an elongate body comprising a length between first and second ends, a width, and a thickness, forming a guide body in the elongate body, bending the elongate body such that first and second lengths of the elongate body oppose each other to form an interior space, and bending the guide body to extend into the interior space.

24 Claims, 13 Drawing Sheets

Related U.S. Application Data filed on May 14, 2020, provisional application No. 62/958,782, filed on Jan. 9, 2020, provisional application No. 62/958,041, filed on Jan. 7, 2020.

(51) Int. Cl.
  *A61B 1/273* (2006.01)
  *A61B 1/05* (2006.01)
  *A61B 1/06* (2006.01)
  *A61B 1/12* (2006.01)

(52) U.S. Cl.
  CPC ...... *A61B 1/00087* (2013.01); *A61B 1/00096* (2013.01); *A61B 1/00098* (2013.01); *A61B 1/00103* (2013.01); *A61B 1/00105* (2013.01); *A61B 1/00121* (2013.01); *A61B 1/053* (2013.01); *A61B 1/0623* (2013.01); *A61B 1/0676* (2013.01); *A61B 1/121* (2013.01); *A61B 1/00177* (2013.01); *A61B 1/2736* (2013.01); *A61B 2505/05* (2013.01)

(58) Field of Classification Search
  CPC ............ A61B 1/00103; A61B 1/00105; A61B 1/0011; A61B 1/00121; A61B 1/053; A61B 1/0623; A61B 1/0676; A61B 1/121; A61B 1/00177; A61B 1/2736; A61B 2505/05
  See application file for complete search history.

(56) References Cited

U.S. PATENT DOCUMENTS

| | | |
|---|---|---|
| 6,459,926 B1 | 10/2002 | Nowlin et al. |
| 8,475,360 B2 | 7/2013 | Brown |
| 9,198,719 B2 | 12/2015 | Murdeshwar et al. |
| 2010/0241087 A1* | 9/2010 | Moulton ........... A61M 25/0612 604/263 |
| 2012/0197081 A1* | 8/2012 | Kimura .............. A61B 1/00124 600/110 |
| 2014/0024897 A1* | 1/2014 | Inoue ................ A61B 1/00154 600/114 |
| 2018/0064318 A1* | 3/2018 | Kitano ................... A61B 1/045 |

FOREIGN PATENT DOCUMENTS

| | | |
|---|---|---|
| EP | 1302151 B1 | 5/2005 |
| WO | WO-2007130711 A1 | 11/2007 |
| WO | WO-2021141755 A1 | 7/2021 |

OTHER PUBLICATIONS

"International Application Serial No. PCT/US2020/065965, Invitation to Pay Additional Fees dated Mar. 3, 2021", 10 pgs.

"International Application Serial No. PCT/US2020/065965, Written Opinion dated Apr. 29, 2021", 10 pgs.

"International Application Serial No. PCT US2020 065965, International Preliminary Report on Patentability dated Jul. 21, 2022", 12 pgs.

* cited by examiner

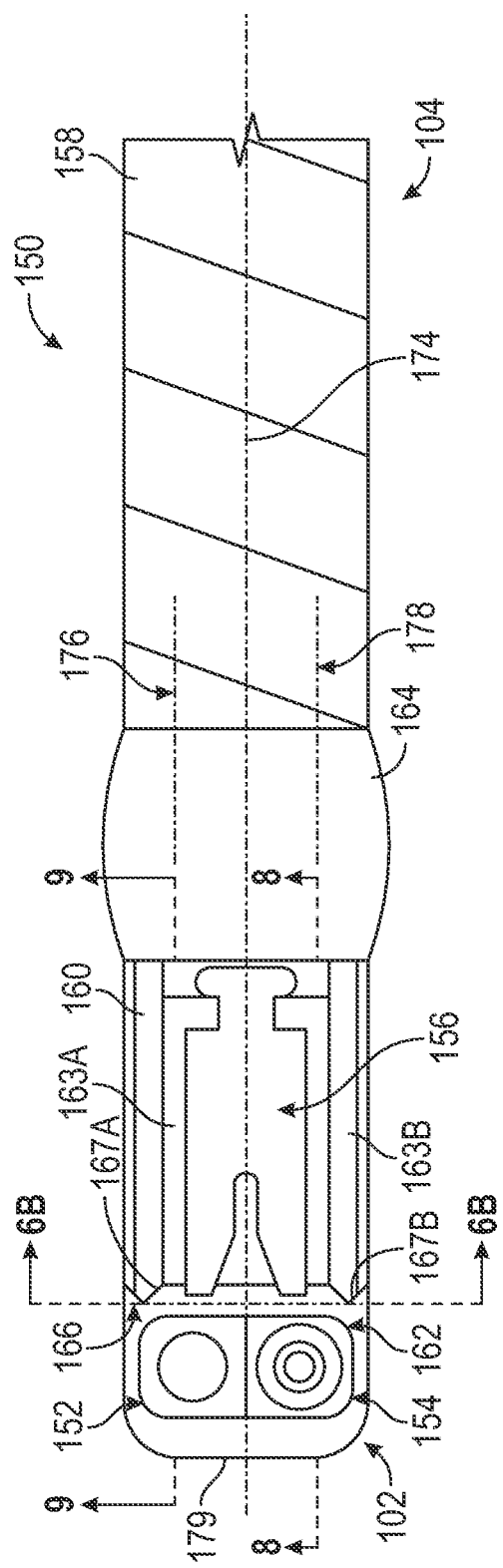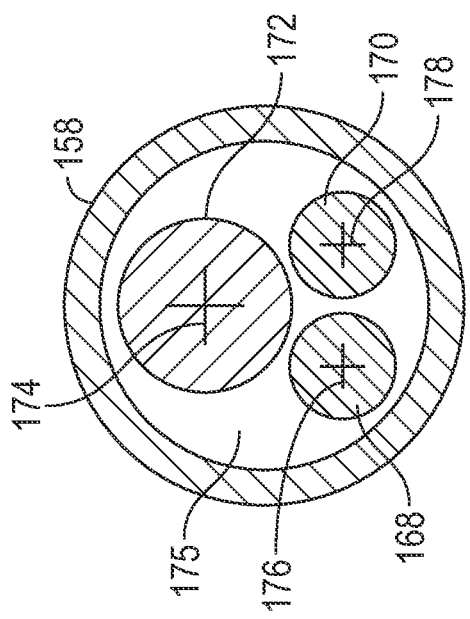
FIG. 6A
FIG. 6B

ONE-PIECE ELEVATOR FOR A DUODENOSCOPE

CROSS-REFERENCE TO RELATED APPLICATIONS

This patent application claims the benefit of priority to U.S. Provisional Patent Application No. 62/958,041 filed Jan. 7, 2020, titled "Endoscope With Low-Profile Distal Section"; U.S. Provisional Patent Application No. 62/958,782 filed Jan. 9, 2020, titled "Endoscope with an Elevator"; U.S. Provisional Patent Application No. 63/024,674 filed May 14, 2020 titled "Endoscope With Low-Profile Distal Section"; and U.S. Provisional Patent Application No. 63/024,682 filed May 14, 2020, titled "One-Piece Elevator For A Duodenoscope"; the entire contents of which are hereby incorporated by reference.

TECHNICAL FIELD

The present disclosure relates generally to medical devices comprising elongate bodies configured to be inserted into incisions or openings in anatomy of a patient to provide diagnostic or treatment operations.

More specifically, the present disclosure relates to endoscopes for imaging and/or providing passage of therapeutic devices toward various anatomical portions, including gastrointestinal tract (e.g., esophagus, stomach, duodenum, pancreaticobiliary duct, intestines, colon, and the like), renal area (e.g., kidney(s), ureter, bladder, urethra) and other internal organs (e.g., reproductive systems, sinus cavities, submucosal regions, respiratory tract), and the like.

BACKGROUND

Conventional endoscopes can be involved in a variety of clinical procedures, including, for example, illuminating, imaging, detecting and diagnosing one or more disease states, providing fluid delivery (e.g., saline or other preparations via a fluid channel) toward an anatomical region, providing passage (e.g., via a working channel) of one or more therapeutic devices for sampling or treating an anatomical region, and providing suction passageways for collecting fluids (e.g., saline or other preparations) and the like. In conventional endoscopy, the distal portion of the endoscope can be configured for supporting and orienting a therapeutic device, such as with the use of an elevator. However, such distal portions can, in a few instances, lead to difficulty in sterilizing or reprocessing the distal portion after use. For example, conventional endoscopy devices can be completely reusable such that crevices between components or spaces within functional components of the distal portion can be difficult to access and clean.

SUMMARY

The present inventors have recognized that problems to be solved with conventional medical devices, and in particular endoscopes and duodenoscopes, include, among other things, particularly those that are difficult or not configured to be easily disassembled, 1) the need and difficulty of cleaning and sterilizing endoscopes after usage, 2) the cost of maintaining multiple endoscopes in inventory to perform different surgical techniques or therapeutic methods on different patients, and 3) the cost of purchasing medical devices having excess capacity or unwanted capabilities for a particular patient. The present disclosure can help provide solutions to these and other problems by providing systems, devices and methods for designing, building, using and deconstructing modular endoscopes. In particular, the present application is directed to detachable camera modules for medical devices such as endoscopes and duodenoscopes. The camera modules can be configured for reuse after appropriate cleaning and sterilization, while the insertion sheaths and shafts to which they can be configured to connect can be configured for one-time use. As such, more expensive camera components can be modularly attached to inexpensive, disposable insertion sheaths and shafts. Said modular camera components can be configured for cleaning, e.g., by being encapsulated, while the insertion sheath and shafts can be inexpensively made to perform only the desired procedure and then disposed of after use. Such configurations can eliminate the need to clean in difficult to reach places in fully assembled devices and the need to maintain a large inventory of devices with different or excess capabilities.

The present inventors have also recognized that problems to be solved with conventional medical devices, and in particular endoscopes and duodenoscopes, include, among other things, the complexity of some components that can lead to increased difficulty in cleaning. In order to avoid difficult cleaning processes, it can be desirable to make such components disposable. As such, it is desirable to make such disposable components less expensive. The present disclosure can help provide solutions to these and other problems by providing systems, devices and methods comprising an elevator for side viewing duodenoscopes, and other devices, that is simple in design and therefore less expensive and easier to make than conventional elevator mechanisms.

The present inventors have additionally recognized that problems to be solved with conventional side viewing endoscopes, such as duodenoscopes, include, among other things, the increased size of the distal end of the device due to the presence of an elevator, which is typically located next to, i.e., radially relative to the longitudinal axis of the device, thereby increasing the diameter of the device. Increased size of the distal end of the device can make it difficult to navigate the device through anatomy of a patient, particularly when faced with small sized orifices or anatomic passageways that intersect at acute angles. The present disclosure can help provide solutions to these and other problems by providing systems, devices and methods comprising side-viewing endoscopes that position imaging and illumination units distal of the elevator mechanism, thereby allowing for smaller distal ends of such medical devices compared to typical duodenoscopes.

In an example, an endoscope can comprise a proximal section, an insertion section extending longitudinally from the proximal section and comprising an elongate tubular body disposed along an insertion section longitudinal axis and a lumen extending through the elongate tubular body, and a distal section extending from the insertion section and comprising an elevator portion comprising an elevator configured to position and orient one or more endotherapy tools extending from the lumen, and a camera module comprising an illumination unit and an imaging unit, the camera module being positioned longitudinally spaced apart from the elevator portion in an in-line configuration, such that the insertion tube longitudinal axis passes through the elevator portion and the camera module.

In another example, an endoscope can comprise a proximal section, an insertion section extending longitudinally from the proximal section and comprising an elongate tubular body disposed along an insertion section longitudinal axis, and a lumen extending through the elongate tubular body, and a distal section extending from the insertion section and comprising an elevator portion comprising an elevator configured to position and orient one or more endotherapy tools extending from the lumen, and a camera module comprising an illumination unit and an imaging unit, the camera module being user-detachable from the elevator portion.

In an additional example, a method of processing modular endoscope components for performing a surgical procedure can comprise identifying a specific patient to receive a specific treatment, selecting an insertion sheath to deliver the specific treatment, attaching a camera module to the insertion sheath, treating the specific patient with the insertion sheath having the attached camera module, and deconstructing the components of the modular endoscope into reusable and disposable components.

BRIEF DESCRIPTION OF DRAWINGS

FIG. 6A is a schematic view of a first example of a low-profile, side-viewing endoscope of the present disclosure comprising side-by-side illumination and imaging units relative to an elevator portion.

FIG. 6B is a schematic cross-sectional view of the endoscope of FIG. 6A taken at plane 6B-6B showing illumination and imaging unit passageways located aside an insertion passageway.

DETAILED DESCRIPTION

Figure 1:
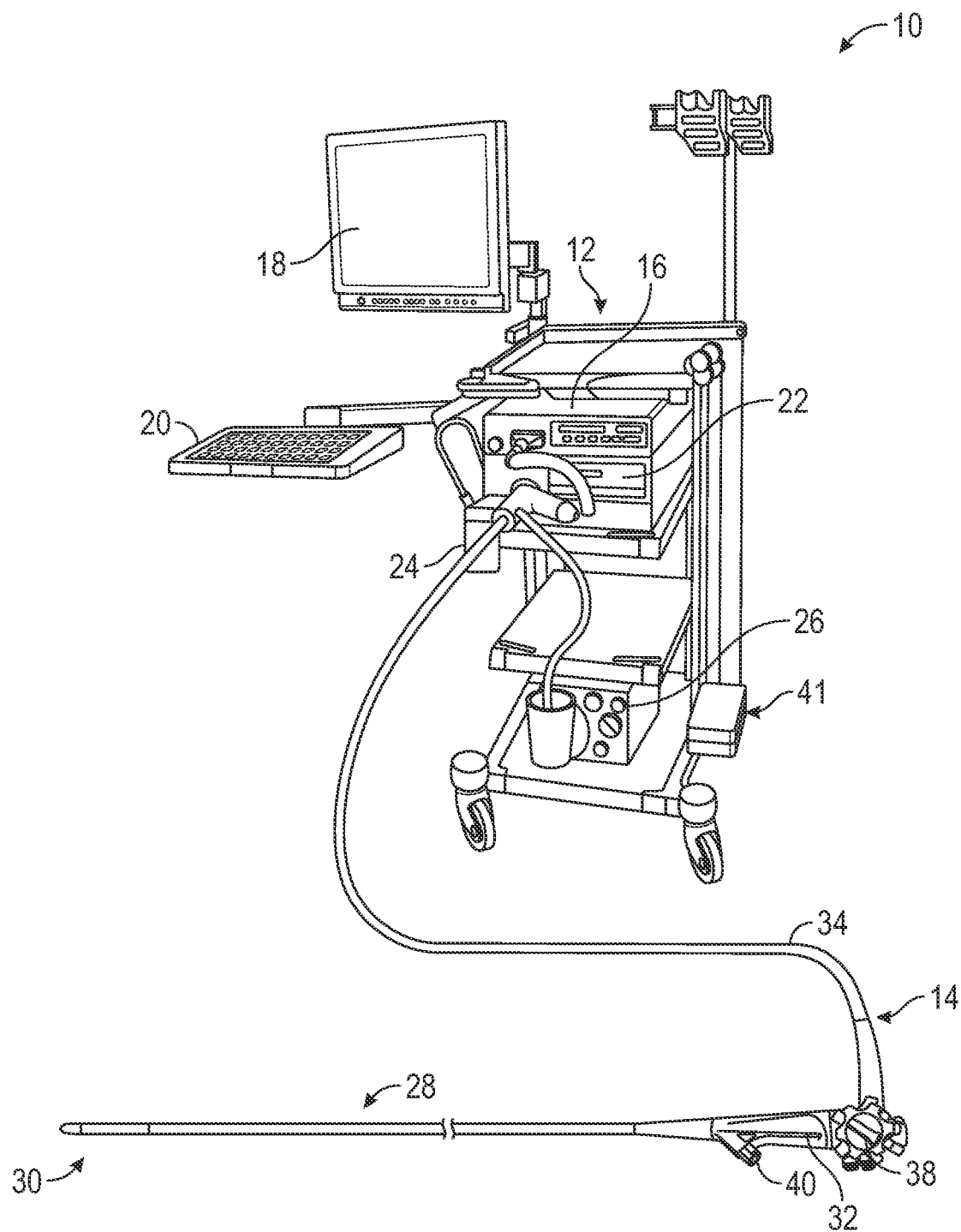
FIG. 1 is a schematic diagram of an endoscopy system comprising an imaging and control system and an endoscope, such as duodenoscope.

FIG. 1 is a schematic diagram of endoscopy system 10 comprising imaging and control system 12 and endoscope 14. FIG. 1 an illustrative example of an endoscopy system suitable for use with the systems, devices and methods described herein, such as modular endoscopy systems, modular endoscopes and methods for designing, building and deconstructing endoscopes. According to some examples, endoscope 14 can be insertable into an anatomical region for imaging and/or to provide passage of one or more sampling devices for biopsies, or one or more therapeutic devices for treatment of a disease state associated with the anatomical region. Endoscope 14 can, in advantageous aspects, interface with and connect to imaging and control system 12. In the illustrated example, endoscope 14 comprises a duodenoscope, though other types of endoscopes can be used with the features and teachings of the present disclosure.

Imaging and control system 12 can comprise controller 16, output unit 18, input unit 20, light source 22, fluid source 24 and suction pump 26.

Imaging and control system 12 can include various ports for coupling with endoscopy system 10. For example, controller 16 can include a data input/output port for receiving data from and communicating data to endoscope 14. Light source 22 can include an output port for transmitting light to endoscope 14, such as via a fiber optic link. Fluid source 24 can include a port for transmitting fluid to endoscope 14. Fluid source 24 can comprise a pump and a tank of fluid or can be connected to an external tank, vessel or storage unit. Suction pump 26 can comprise a port used to draw a vacuum from endoscope 14 to generate suction, such as for withdrawing fluid from the anatomical region into which endoscope 14 is inserted. Output unit 18 and input unit 20 can be used by an operator of endoscopy system 10 to control functions of endoscopy system 10 and view output of endoscope 14. Controller 16 can additionally be used to generate signals or other outputs from treating the anatomical region into which endoscope 14 is inserted. In examples, controller 16 can generate electrical output, acoustic output, a fluid output and the like for treating the anatomical region with, for example, cauterizing, cutting, freezing and the like.

Endoscope 14 can comprise insertion section 28, functional section 30 and handle section 32, which can be coupled to cable section 34 and coupler section 36.

Insertion section 28 can extend distally from handle section 32 and cable section 34 can extend proximally from handle section 32. Insertion section 28 can be elongate and include a bending section, and a distal end to which functional section 30 can be attached. The bending section can be controllable (e.g., by control knob 38 on handle section 32) to maneuver the distal end through tortuous anatomical passageways (e.g., stomach, duodenum, kidney, ureter, etc.). Insertion section 28 can also include one or more working channels (e.g., an internal lumen) that can be elongate and support insertion of one or more therapeutic tools of functional section 30. The working channel can extend between handle section 32 and functional section 30. Additional functionalities, such as fluid passages, guide wires, and pull wires can also be provided by insertion section 28 (e.g., via suction or irrigation passageways, and the like).

Handle module 32 can comprise knob 38 as well as ports 40. Knob 38 can be coupled to a pull wire extending through insertion section 28. Ports 40 can be configured to couple various electrical cables, fluid tubes and the like to handle module 32 for coupling with insertion section 28.

Imaging and control system 12, according to examples, can be provided on a mobile platform (e.g., cart 41) with shelves for housing light source 22, suction pump 26, image processing unit 42, etc. Alternatively, several components of imaging and control system 12 shown in FIGS. 1 and 2 can be provided directly on endoscope 14 so as to make the endoscope "self-contained."

Figure 2:
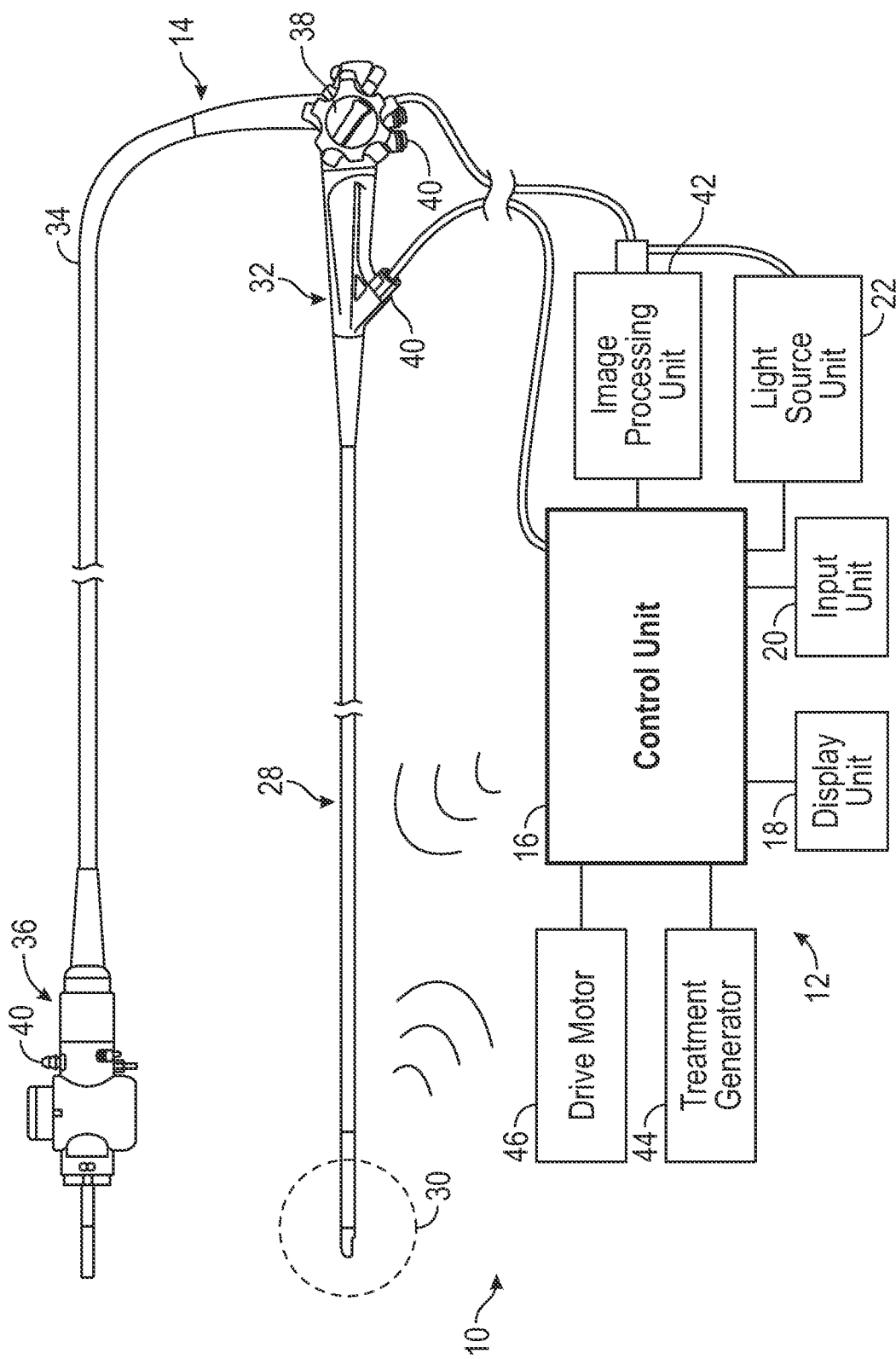
FIG. 2 is a schematic diagram of the endoscopy system of FIG. 1 comprising the endoscope connected to a control unit of the imaging and control system.

FIG. 2 is a schematic diagram of endoscopy system 10 of FIG. 1 comprising imaging and control system 12 and endoscope 14. FIG. 2 schematically illustrates components of imaging and control system 12 coupled to endoscope 14, which in the illustrated example comprises a duodenoscope. Imaging and control system 12 can comprise controller 16, which can include or be coupled to image processing unit 42, treatment generator 44 and drive unit 46, as well as light source 22, input unit 20 and output unit 18.

Image processing unit 42 and light source 22 can each interface with endoscope 14 by wired or wireless electrical connections. Imaging and control system 12 can accordingly illuminate an anatomical region, collect signals representing the anatomical region, process signals representing the anatomical region, and display images representing the anatomical region on display unit 18. Imaging and control system 12 can include light source 22 to illuminate the anatomical region using light of desired spectrum (e.g., broadband white light, narrow-band imaging using preferred electromagnetic wavelengths, and the like). Imaging and control system 12 can connect (e.g., via an endoscope connector) to endoscope 14 for signal transmission (e.g., light output from light source, video signals from imaging system in the distal end, and the like).

Fluid source 24 can comprise one or more sources of air, saline or other fluids, as well as associated fluid pathways (e.g., air channels, irrigation channels, suction channels) and connectors (barb fittings, fluid seals, valves and the like). Imaging and control system 12 can also include drive unit 46, which can be an optional component. Drive unit 46 can comprise a motorized drive for advancing a distal section of endoscope 14, as described in at least PCT Pub. No. WO 2011/140118 A1 to Frassica et al., titled "Rotate-to-Advance Catheterization System," which is hereby incorporated in its entirety by this reference.

Figure 3:
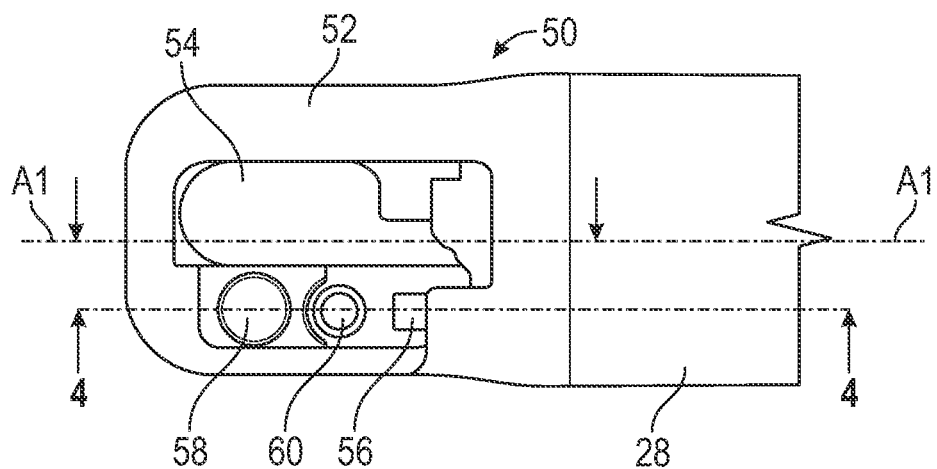
FIG. 3 is a schematic top view of a camera module including optical components for a side-viewing endoscope.
Figure 4:
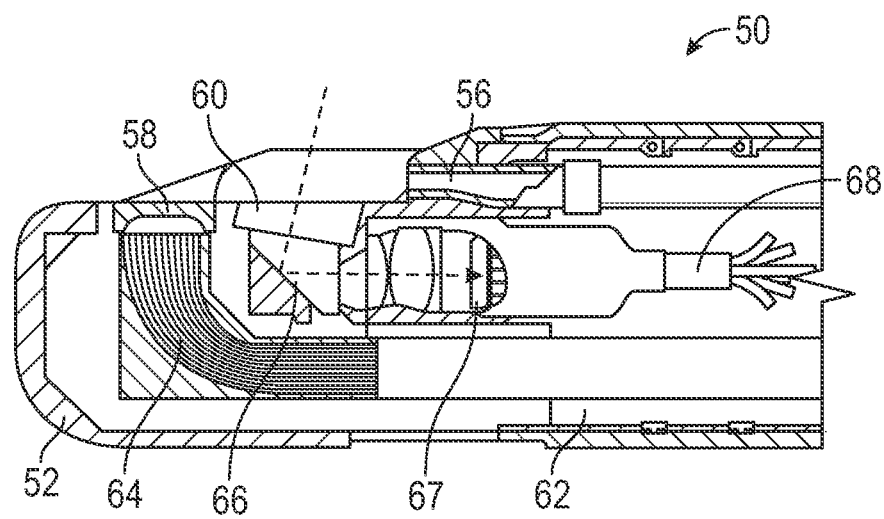
FIG. 4 is an enlarged cross-sectional view taken at plane 4-4 of FIG. 3 showing the optical components.

FIGS. 3 and 4 illustrate a first example of functional section 30 of endoscope 14 of FIG. 2. FIG. 3 illustrates a top view of functional section 30 and FIG. 4 illustrates a cross-sectional view of functional section 30 taken along section plane 3-3 of FIG. 3. FIGS. 3 and 4 each illustrate "side-viewing endoscope" (e.g., duodenoscope) camera module 50. In side-viewing endoscope camera module 50, illumination and imaging systems are positioned such that the viewing angle of the imaging system corresponds to a target anatomy lateral to central longitudinal axis A1 of endoscope 14.

In the example of FIGS. 3 and 4, side-viewing endoscope camera module 50 can comprise housing 52, elevator 54, fluid outlet 56, illumination lens 58 and objective lens 60. Housing 52 can form a fluid tight coupling with insertion section 28. Housing 52 can comprise opening for elevator 54. Elevator 54 can comprise a mechanism for moving a device inserted through insertion section 28. In particular, elevator 54 can comprise a device that can bend an elongate device extended through insertion section 28 along axis A1. Elevator 54 can be used to bend the elongate device at an angle to axis A1 to thereby treat the anatomical region adjacent side-viewing endoscope camera module 50. Without regard to the detachable camera module capabilities and disposable elevator portion constructions described herein that can be used with camera module 50, camera module comprises a conventional orientation of elevator 54 relative to illumination lens 58 and objective lens 60.

As can be seen in FIG. 4, insertion section 28 can comprise central lumen 62 through which various components can be extended to connect functional section 30 with handle section 32 (FIG. 2). For example, illumination lens 58 can be connected to light transmitter 64, which can comprise a fiber optic cable or cable bundle extending to light source 22 (FIG. 1). Likewise, objective lens 60 can be coupled to prism 66 and imaging unit 67, which can be coupled to wiring 68. Also, fluid outlet 56 can be coupled to fluid line 69, which can comprise a tube extending to fluid source 24 (FIG. 1). Other elongate elements, e.g., tubes, wires, cables, can extend through lumen 62 to connect functional section 30 with components of endoscopy system 10, such as suction pump 26 (FIG. 1) and treatment generator 44 (FIG. 2).

Side-viewing endoscope camera module 50 of FIGS. 3 and 4 can include optical components (e.g., objective lens 60, prism 66, imaging unit 67, wiring 68) for collection of image signals, lighting components (e.g., illumination lens 58, light transmitter 64) for transmission or generation of light. Endoscope camera module 50 can also include a photosensitive element, such as a charge-coupled device ("CCD" sensor) or a complementary metal-oxide semiconductor ("CMOS") sensor. In either example, imaging unit 67 can be coupled (e.g., via wired or wireless connections) to image processing unit 42 (FIG. 2) to transmit signals from the photosensitive element representing images (e.g., video signals) to image processing unit 42, in turn to be displayed on a display such as output unit 18. In various examples, imaging and control system 12 and image processing unit 67 can be configured to provide outputs at desired resolution (e.g., at least 480p, at least 720p, at least 1080p, at least 4K UHD, etc.) suitable for endoscopy procedures.

As mentioned, the present inventors have recognized that conventional endoscopes, particularly, duodenoscopes, can include elevator sections that comprise elaborate and intricate constructions that can be expensive and difficult to clean. The present inventors have developed solutions to these and other problems by developing endoscopes that can have detachable, low-profile camera modules, including illuminating and imaging components, that can be separated from a disposable insertion section sheath having an easy to produce and inexpensive elevator design. As such, the camera module can include high-quality or high-performance imaging components that can be reused and enveloped in an easy to clean housing. For example, the cameral module can include a 4K, high-imaging unit that can be contained in a sealed container having cut-outs or windows for imaging and illumination lenses, thereby eliminating or reducing cracks and crevices for biological matter to become lodged. Furthermore, the elevator mechanism can comprise a flat, sheet metal structure stamped and formed to attached to a disposable insertion sheath that can be easily cleaned if desired due to simple geometry or disposed of without significant cost due to simple construction.

Figure 5:
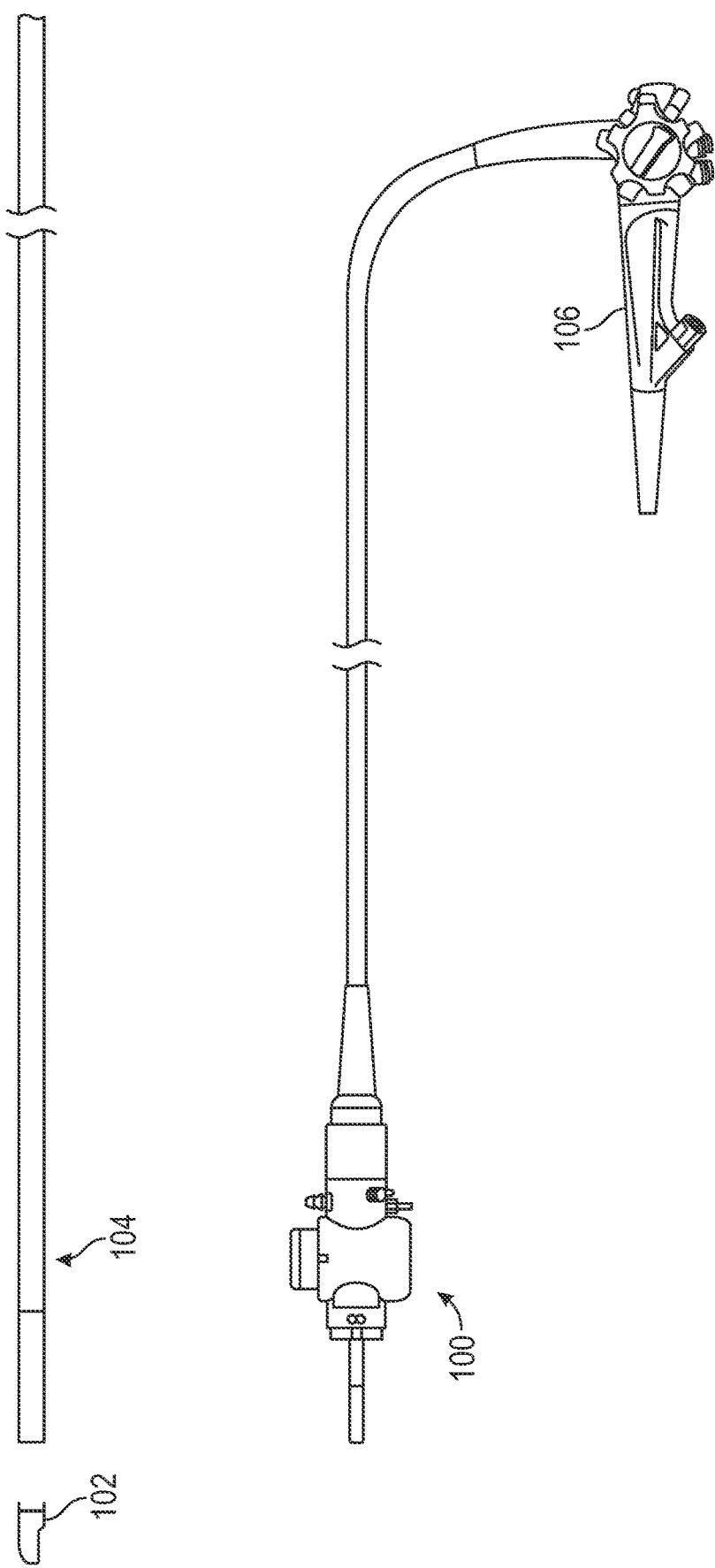
FIG. 5 is a schematic view of a modular endoscope suitable for use as the endoscope of FIGS. 1-4 comprising a camera module, an insertion section module, and a navigation and control module that are configured to be detachable from each other.

FIG. 5 is a schematic view of modular endoscope 100 suitable for use as endoscope 14 and with endoscope camera module 50 of FIGS. 3 and 4. Modular endoscope 100 can comprise a modular detachable functional module 102, insertion section module 104 and navigation and control module 106. Modules 102, 104 and 106 can comprise components including customizable features and components. As such, modular endoscope 100 can be custom-built to perform a specific procedure for a specific patient. Individual modular components can be configured as reusable or disposable components. Therefore, inexpensive or difficult to clean components can be disposed of and expensive or easy to clean components can be reused after appropriate cleaning and sterilizing.

Functional module 102 can comprise functional module 30, camera module 50 or other types of modules. Functional module 30 can include one or both of an imaging device, a therapeutic device, and an ancillary therapeutic device, as well as other devices as is described herein. Furthermore, functional module 102 can comprise camera module 162 of endoscope 150 of FIGS. 6A and 6B and camera module 192 of endoscope 180 of FIGS. 7A and 7B.

Insertion section module 104 can comprise insertion section 28, which can be configured to include one or more of the sheath and shaft components of U.S. 63/017,901 filed on Apr. 30, 2020, titled, "Insertion Sheath for Modular Endoscope with Detachable and Selectively Disposable Components," the entire contents of which is hereby incorporated by reference.

Navigation and control module 106 can comprise handle section 32, cable section 34 and coupler section 36 of FIGS. 1 and 2.

As mentioned previously, components of endoscope 14 can be modular such that they can be attached by an operator to initially configure the device for use with a patient, and can be detached by the operator after use with the patient. In other examples, the modular components can be assembled and disassembled by a manufacturer or a decommissioning service without action from the operator. In an example, FIG. 5 illustrates endoscope 14 of FIG. 2, wherein components thereof are shown in a detached state. While FIG. 5 illustrates endoscope 14 as being constructed from three modular components (functional module 102 [functional section 30], navigation and control module 106 [handle section 32], insertion section module 104 [insertion section 28]), additional or fewer components are contemplated, depending on the surgical procedure to be performed with the embodiment of endoscope 14 constructed or designed by the operator. Each of functional module 102, navigation and control module 106, and insertion section module 104 can be detachable from each other. Furthermore, each of modules 102, 104 and 106 can be disposed after a single clinical use. Alternatively, each of modules 102, 104 and 106 can be constructed using materials that would permit several clinical uses. In such cases, modules 102, 104 and 106 can be constructed to withstand sterilization after each clinical use.

In certain advantageous aspects, the modular construction of endoscope 14 of FIGS. 2 and 5, and as discussed herein, can permit mixing and matching of disposable and reusable modules such that some modules can be reused, such as expensive and/or easy to clean modules, and some modules can be disposable, such as simple and/or difficult to clean modules. For example, certain modules can be detached from the endoscope after a clinical use for sterilization, reprocessing, and reuse for subsequent clinical uses, while the remaining modules can be disposed. For instance, there have been concerns with inadequate reprocessing of portions of duodenoscopes (e.g., elevator portions). As a result, single-use endoscopes that can be disposed after a single clinical use (to prevent infection between uses) have been developed. However, currently available single-use endoscopes, wherein the entire endoscope is disposed of, can be constructed using lower cost materials resulting in a lower price for the endoscope in order to remain competitive per clinical use. In many clinical instances, lower cost materials can lead to poorer clinical performance (e.g., lower quality images, inadequate maneuverability, insertion section module damage during insertion, poorer ergonomic of endoscope handle, etc.). As such, inferior components can result in practitioners preferring not to use such devices.

Accordingly, modular endoscope 14 of FIGS. 2 and 5, and others described herein (e.g., endoscopes 150 and 18), is advantageously constructed such that the end user (e.g., health care providers and facilities) can recover certain modules of endoscope 14 for reuse, while disposing infection prone areas after a single clinical use. In addition, portions of the endoscope that are intended for reuse can be constructed to reduce accumulation of biological materials (such as be being fully encapsulated), and can additionally be fluidly isolated from infection prone areas. Such configurations promote the use of a combination of higher quality (higher cost) reusable components usable over multiple clinical uses, and lower cost, disposable portions, while reducing infection risk, and achieving desired clinical performance. Not only can the disposable components be constructed to include features only needed for the specifically-built procedure, but the materials and construction can be built to only survive one-time use, both of which help reduce the cost of the disposable components. For example, insertion sheaths can be built to survive the stress of only a single operation and does not need to be robustly constructed to survive repetitive stresses of multiple procedures.

In examples, endoscope 100 of FIG. 5 can comprise a duodenoscope, functional module 102 can be configured as a reusable camera module, navigation and the control module 106 can comprise a reusable handle module, and insertion section module 104 can comprise a disposable unit having multiple lumens. Accordingly, the camera module and the navigation and control module can each include connectors that can maintain each of the camera module and the navigation and control module in an attached state to the insertion section module during use with a patient. After each use, the camera module and the navigation and control module can be separated (e.g., using the connectors such as attachment mechanism 240 of FIG. 10), and reprocessed for subsequent use with a new insertion section module. Conversely, the used insertion section module can be disposed after a single use.

Additionally, the connectors of the camera module and the navigation and the control module as well as the camera module and the navigation and the control module can be constructed of materials and engineered to reduce any ingress of biological materials and may optionally be constructed in a fluid-tight manner.

Modular endoscope 100 can be configured for either a "side-viewing" configuration (as shown in FIGS. 3 and 4) or an "end-viewing" configuration, as is conventionally known (such as a gastroscope, colonoscope, cholangioscope, etc.). In examples, wherein modular endoscope 100 is configured as a side-viewing device (e.g., side-viewing duodenoscope), the illumination unit and the imaging unit of the distal modular section (e.g., camera module) can both be offset from a longitudinal axis (e.g., axis 174 of FIG. 6A) of the insertion section module (FIGS. 6A and 6B), or the illumination unit and the imaging unit of the distal modular section (e.g., camera module) can both be aligned with a longitudinal axis (e.g., axis 204 of FIG. 7A) of the insertion section module (FIGS. 7A and 7B) to facilitate a low-profile of the device.

FIG. 6A is a schematic view of low-profile, side-viewing endoscope 150 of the present disclosure comprising illumination unit 152 and imaging unit 154 arranged in a side-by-side configuration relative to elevator portion 156. Endoscope 150 can comprise sheath 158, elevator housing 160, camera module 162 and fluid passageways 163A and 163B. Band 164 can be disposed adjacent sheath 158 and elevator housing 160 to facilitate coupling and sealing therebetween. Camera module 162 can be coupled to elevator housing 160 at joint line 166 using, for example, attachment mechanism 240 of FIG. 10.

Fluid passageways 163A and 163B can comprise tubes or conduits that can connect nozzles 167A and 167B to fluid source 24 (FIG. 1) or another fluid source. Proximal ends of fluid passageways 163A and 163B can be connected to air or liquid sources (e.g., fluid source 24 of FIG. 1) for dispensing one or both of compressed air and saline or other liquids for cleaning functionalities, such as to remove debris or biological matter from illumination unit 152 and imaging unit 154.

Fluid passageways 163A and 163B can be positioned on opposite sides of elevator portion 156 such that nozzle 167A is directed toward illumination unit 152 and nozzle 167B is directed toward imaging unit 154. Fluid passageways 163A and 163B can be disposed in a direction that extends generally parallel to longitudinal axis 174. However, in other configurations fluid passageways 163A and 163B can be disposed to direct nozzles 167A and 167B in other directions. In the illustrated example, fluid passageways 163A and 163B comprise circular conduits connected to nozzles 167A and 167B. However, in other examples, fluid passageways 163A and 163B can have other cross-sectional shapes and nozzles 167A and 167B can have other configurations, such as jets or circular orifices. As is discussed with reference to FIG. 7A6, in other configurations, a single fluid passageway and nozzle can be used.

FIG. 6B is a schematic cross-sectional view of endoscope 150 of FIG. 6A taken at plane 6B-6B showing illumination unit passageway 168 and imaging unit passageway 170 located radially aside insertion passageway 172. Insertion passageway 172 can extend along central axis 174 within space 175 of sheath 158. Illumination unit passageway 168 and imaging unit passageway 170 can extend along central axes 176 and 178, respectively, within space 175 of sheath 158.

Figure 7A:
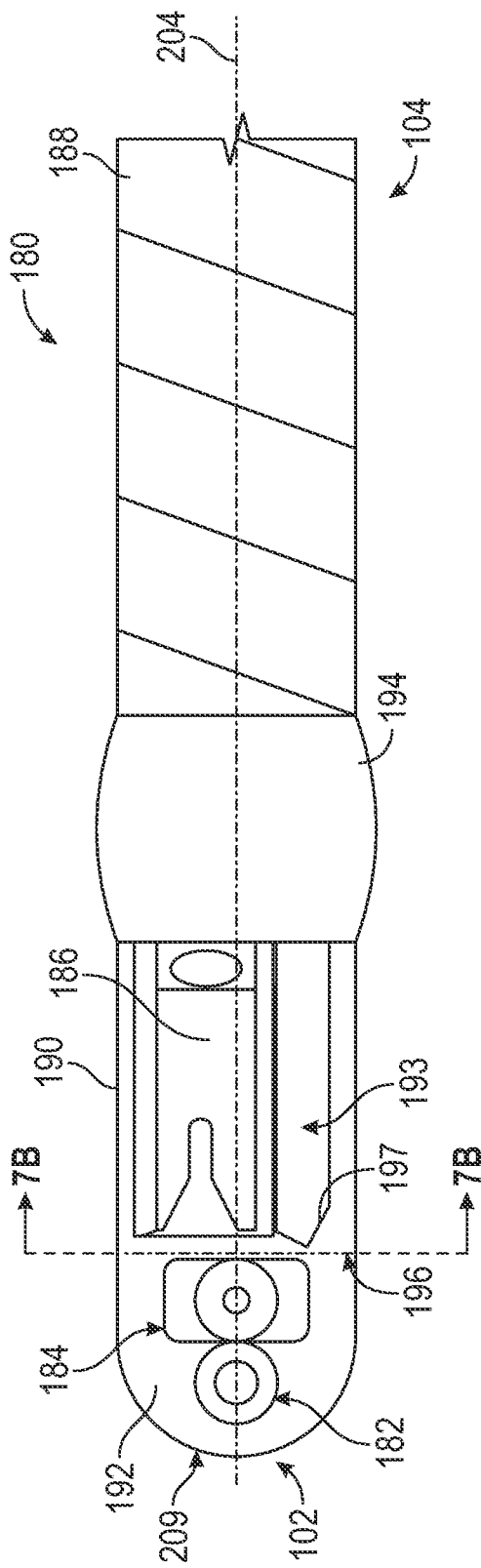
FIG. 7A is a schematic view of a second example of a low-profile, side-viewing endoscope of the present disclosure comprising end-to-end illumination and imaging units relative to an elevator portion.

FIG. 7A is a schematic view of low-profile, side-viewing endoscope 180 of the present disclosure comprising illumination unit 182 and imaging unit 184 arranged in an end-to-end configuration relative to elevator portion 186. Endoscope 180 can comprise sheath 188, elevator housing 190, camera module 192 and fluid passageway 193. Band 194 can be disposed adjacent sheath 188 and elevator housing 190. Camera module 192 can be coupled to elevator housing 190 at joint line 196 using, for example, attachment mechanism 240 of FIG. 10.

Fluid passageway 193 can comprise a tube or conduit that can connect nozzle 197 to fluid source 24 (FIG. 1) or another fluid source. Proximal ends of fluid passageway 193 can be connected to air or liquid sources (e.g., fluid source 24 of FIG. 1) for dispensing one or both of compressed air and saline or other liquids for cleaning functionalities, such as to remove debris or biological matter from illumination unit 182 and imaging unit 184. Fluid passageways 193 can be positioned on one side of elevator portion 186 such that nozzle 197 is directed toward illumination unit 182 and imaging unit 184. Fluid passageway 193 can be disposed in a direction that extends generally parallel to longitudinal axis 204, with nozzle 197 being angled relative to fluid passageway 193 to aim fluid or liquid toward camera module 192. However, in other configurations fluid passageway 193 can be disposed to direct nozzle 197 in other directions. In the illustrated example, fluid passageway 193 comprises a circular conduit connected to nozzle 197. However, in other examples, fluid passageway 193 can have other cross-sectional shapes and nozzle 197 can have other configurations, such as a jet or circular orifice. Placement of only a single passageway (e.g., fluid passageway 193) with a single nozzle (e.g., nozzle 197) to one side of elevator portion 186 can lead to a low-profile architecture of the distal portion in comparison to the distal portion of FIG. 6A.

Figure 7B:
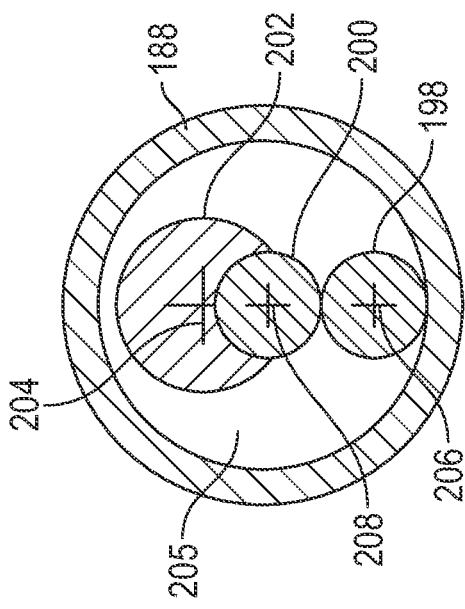
FIG. 7B is a schematic cross-sectional view of the endoscope of FIG. 7A taken at plane 7B-7B showing illumination and imaging unit passageways aligned with an insertion passageway.

FIG. 7B is a schematic cross-sectional view of endoscope 180 of FIG. 7A taken at plane 7B-7B showing illumination unit passageway 198 and imaging unit passageway 200 located radially aligned with insertion passageway 202. Insertion passageway 202 can extend along central axis 204 within space 205 of sheath 188. Illumination unit passageway 198 and imaging unit passageway 200 can extend along central axis 206 and 208, respectively, within space 205 of sheath 188.

Endoscopes 150 and 180 of FIGS. 6A and 7A each illustrate a distal end of a low-profile endoscope having side-viewing capabilities according to the present disclosure. As shown in FIGS. 6A and 7A, according to some embodiments, elevator portions 156 and 186 and camera modules 162 and 192 can be arranged in axially in-line configurations, respectively.

For instance, with respect to endoscope 150, longitudinal axis 174 of the insertion section module 104 can generally pass through both elevator portion 156 and camera module 162. In the specific example of FIG. 6A, longitudinal axis 174 can pass between illumination unit 152 and imaging unit 154. As can be seen in FIG. 6A, distal-most end surface 179 can form a flat end tip that can be generally planar. For example, end surface 179 can be disposed at an angle generally perpendicular to the longitudinal axis 174.

Likewise, with respect to endoscope 180, longitudinal axis 204 of the insertion section module 104 can generally pass through both elevator portion 186 and camera module 192. In the specific example of FIG. 7A, longitudinal axis 204 can pass through both illumination unit 182 and imaging unit 184. As can be seen in FIG. 7A, distal-most end surface 209 can form a round end tip that can be generally non-planar. For example, end surface 209 can generally have an arcuate shape (e.g., a "bullet nose" shape), and can advantageously be atraumatic.

Accordingly, the arrangements of camera modules 162 and 192 are rotated (e.g., perpendicularly or 90° orientation) from the embodiment shown in FIGS. 3 and 4. In either embodiment, the "axially in-line arrangement" of the camera module and the elevator portion can lead to more-efficient packaging and a compact architecture at the distal end, and reduce the outer diameter of the distal section (e.g., in comparison to the outer diameter of the distal end of the scope illustrated in FIGS. 3 and 4.

Figure 8:
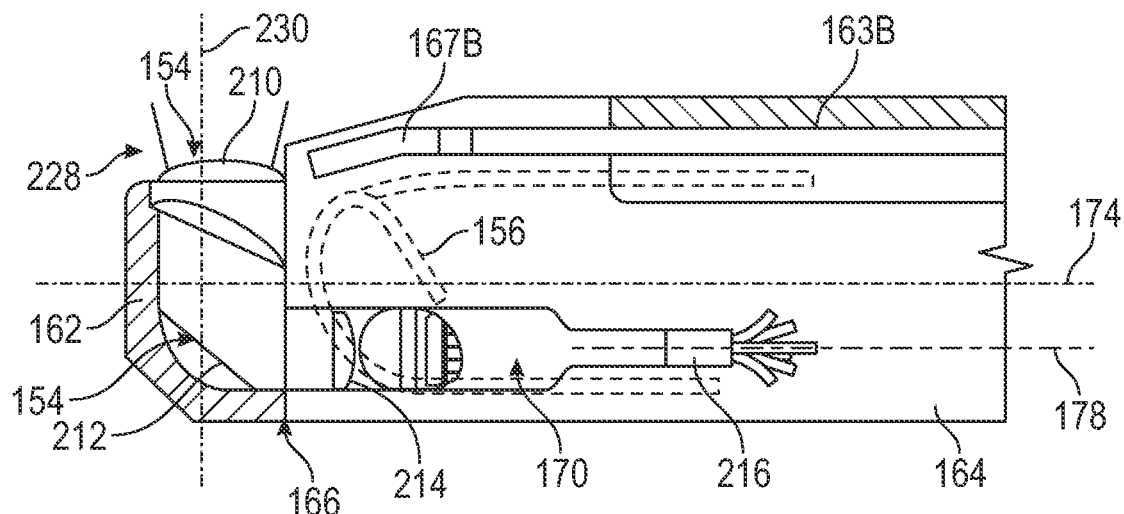
FIG. 8 is a schematic cross-sectional view of the low-profile, side-viewing endoscope of FIG. 6A taken at plane 8-8 showing the imaging unit and the imaging passageway relative to the elevator.
Figure 9:
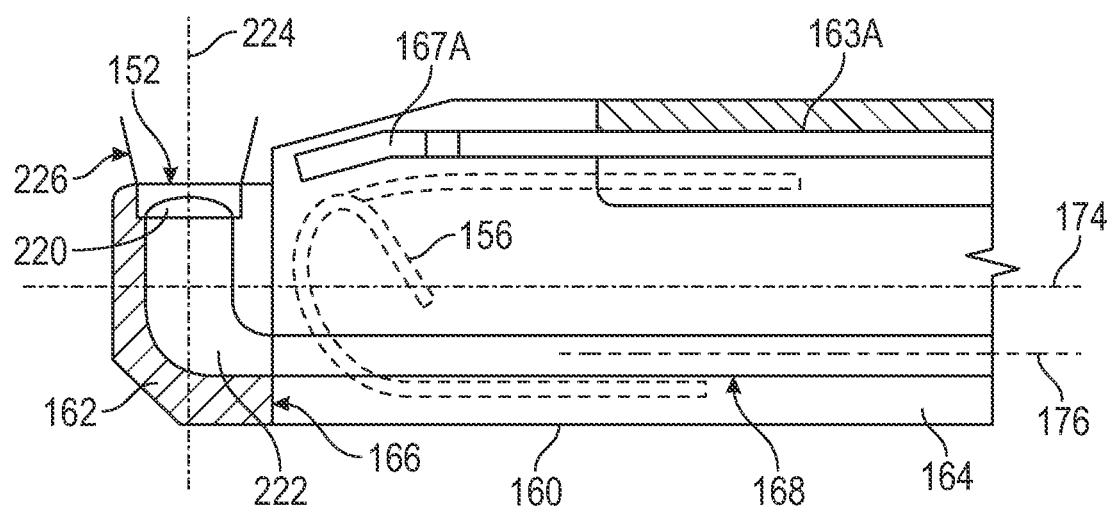
FIG. 9 is a schematic cross-sectional view of the low-profile, side-viewing endoscope of FIG. 6A taken at plane 9-9 showing the illumination unit and the illumination passageway relative to the elevator.

FIGS. 8 and 9 illustrate enlarged sectional views of endoscope 150 illustrated in FIG. 6A. Endoscope 150 can comprise illumination unit 152, imaging unit 154, elevator portion 156, sheath 158, elevator housing 160, camera module 162, fluid passages 163A and 163B, band 164, joint line 166 and nozzles 167A and 167B.

As shown in FIG. 8, imaging unit 154 can comprise imaging unit passageway 170, lens 210, prism 212, photosensitive element 214 and cable 216.

As shown in FIG. 9, illumination unit 152 can comprise illumination unit passageway 168, lens 220 and light conductor 222.

As is discussed in greater detail with reference to FIGS. 13-15, elevator portion 156 can comprise elongate body 300, first end portion 302, second end portion 304, arcuate section 306, guide 308 and portal 310.

FIG. 8 is a schematic cross-sectional view of low-profile, side-viewing endoscope 150 of FIG. 6A taken at plane 8-8 showing imaging unit 152 and imaging unit passageway 170 relative to the elevator portion 156. The sectional plane 8-8 passes through first axis 178 that extends through both imaging unit 154 and elevator portion 156 and is parallel to longitudinal axis 174.

Imaging unit 152 can include, in examples, photosensitive element 214. According to some examples, photosensitive element 214 can be a charge-coupled device ("CCD" sensor). In alternative examples, photosensitive element 214 can be a complementary metal-oxide semiconductor ("CMOS") sensor. In either example, photosensitive element 214 can be coupled (e.g., via wired or wireless connections) to image processing unit 42 (FIG. 2) to transmit signals from photosensitive element 214 representing images (e.g., video signals) to image processing unit 42, in turn to be displayed on a display (e.g., output unit 18 of FIG. 1). In certain examples, imaging processing unit 42 and imaging unit 154 can be configured to provide outputs at desired resolution (e.g., at least 480p, at least 720p, at least 1080p, at least 4K UHD, etc.) suitable for endoscopy procedures.

Imaging unit 154 can be positioned longitudinally in-line with elevator portion 156. Elevator portion 156 can include first end portion 302 and second end portion 304 longitudinally spaced apart by elongate portion 300. Arcuate section 306 of elongate portion 300 can position first end portion 302 and second end portion 304 in an opposing relationship such that each portion extends in the direction of longitudinal axis 174 and interior space 311 is formed therebetween. Accordingly, in the example of FIG. 8, imaging unit 154, including at least one lens including lens 210, can be positioned adjacent arcuate section 306 and spaced apart from first end portion 302 and second end portion 304 of elevator portion 156 in a direction along or parallel to longitudinal axis 174.

According to an embodiment, and with continued reference to FIGS. 6A and 8, while the illustrated examples can be suitable for a variety of endoscopes (including side-viewing and end-viewing endoscopes), in one example, imaging unit 154 (positioned in-line with elevator portion 156) can be advantageously configured to permit side-viewing. Accordingly, imaging unit 154 can include optical components (e.g., lens 210, prism 212, and/or optional optical fibers) to permit viewing a target region in a direction generally non-parallel (e.g., perpendicular) to longitudinal axis 174. FIG. 8 illustrates one example, wherein imaging unit 154 includes objective lens 210, with an optical axis 230 oriented non-parallel (e.g., perpendicular) to first axis 178 passing through imaging unit 154 and elevator portion 156.

Referencing FIGS. 6B and 8, the second axis 176 can be generally parallel to longitudinal axis 174 and the first axis 178 that passes through elevator portion 156 and illumination unit 152. Accordingly, photosensitive element 214 can view (e.g., illustrated by imaging unit field of view 228) a target region along a direction centered on objective lens optical axis 230, and generally non-parallel (e.g., perpendicular) to insertion tube longitudinal axis 174 and first axis 178. In the example of FIG. 8, one or more optical elements (e.g., additional lenses, a roof prism) can optically couple objective lens 210 to photosensitive element 214 (e.g., CCD or CMOS sensor). Photosensitive element 214 can be provided just below imaging lens 210 to realize additional space savings in the distal section of endoscope 150 and to facilitate modular construction of camera module 162.

FIG. 9 is a schematic cross-sectional view of low-profile, side-viewing endoscope 150 of FIG. 6A taken at plane 9-9 showing illumination unit 152 and illumination passageway 172 relative to elevator portion 156. Sectional plane 9-9 passes through second axis 176 that extends through both illumination unit 152 and elevator portion 156 and is parallel to longitudinal axis 174 and first axis 178 (shown in FIG. 8).

Illumination unit 152 can comprise optical components including lens 220 and other optical components and can be connected to light conductor 222. Light conductor 222 can comprise optical fibers or other light guides that can be connected to light source 22 (FIG. 2). As such, illumination unit 152 can be used to illuminate a target region, e.g., a region of anatomy of a patient, with light from light source 22 via light conductor 222. Light source 22 can be connected to a proximal portion of light conductor 22. Alternatively, in other examples, illumination unit 152 can be "self-contained." In such self-contained units, illumination unit 152 can include one or more light sources or lamps, such as light emitting diodes, as well as a power source such as a battery. Illumination unit 152 can be connected to a distal end of light conductor 222. In examples, illumination unit 152 can comprise a portion of a detachable camera module as described in the commonly-assigned U.S. patent application, 62/951,157, titled, "Modular Endoscope with Detachable and Selectively Disposable Components," filed on Dec. 20, 2019, the entire contents of which is hereby incorporated by reference.

Figure 13:
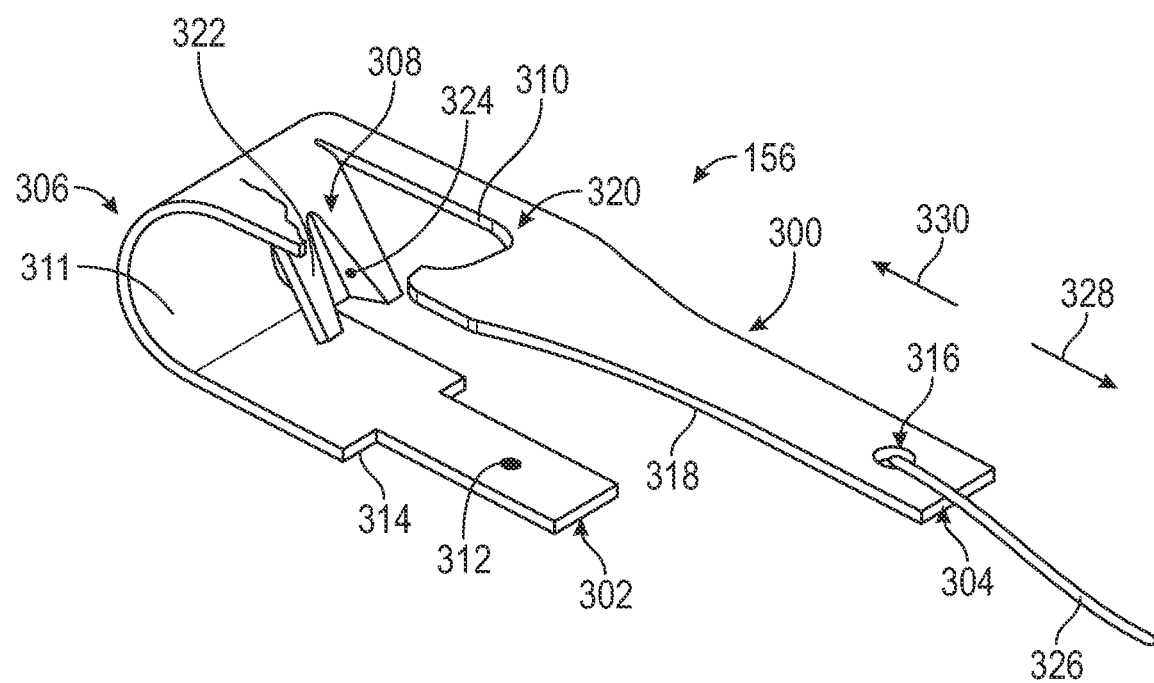
FIG. 13 is a perspective view of an elevator mechanism of the present disclosure suitable for use with disposable, low-profile endoscopes.

With reference to FIGS. 6A, 9 and 13, illumination unit 152 can be positioned longitudinally in-line with elevator portion 156. Elevator portion 156 can include first end portion 302 and second end portion 304 longitudinally spaced apart by elongate portion 300. Arcuate section 306 of elongate portion 300 can position first end portion 302 and second end portion 304 in an opposing relationship such that each portion extends in the direction of longitudinal axis 174 and space 311 is formed therebetween. Accordingly, in the example of FIG. 9, illumination unit 152, including at least one lens including lens 220, can be positioned adjacent arcuate section 306 and spaced apart from first end portion 302 and second end portion 304 of elevator portion 156 in a direction along or parallel to longitudinal axis 174.

According to an embodiment, and with continued reference to FIGS. 6A and 9, while the illustrated examples can be suitable for a variety of endoscopes (including side-viewing and end-viewing endoscopes), in one example, illumination unit 152 (positioned in-line with elevator portion 156) can be advantageously configured to permit side-viewing. Accordingly, illumination unit 152 can include optical components (e.g., lens 220 and/or optional optical fibers) to provide light output in a direction generally non-parallel (e.g., perpendicular) to longitudinal axis 174. FIG. 9 illustrates one example, wherein illumination unit 152 includes illumination lens 220, with optical axis 224 oriented non-parallel (e.g., perpendicular) to second axis 176 passing through the illumination unit and the elevator portion.

Referencing FIGS. 6B and 9, first axis 178 can be generally parallel to longitudinal axis 174 and second axis 176. Accordingly, light from a light source, self-contained within illumination unit 152 or from light source 22 of FIG. 2, can be output from the distal section of endoscope 150 as a light cone 226 centered on illumination lens optical axis 224, and generally non-parallel (e.g., perpendicular) to longitudinal axis 174 and second axis 176. In the example of FIG. 9, light conductor 222 can comprise one or more optical fibers (e.g., fiber bundle) that can optically couple illumination lens 220 to the light source (e.g., provided on light source 22 of FIG. 2) via illumination unit passageway 168 that extends underneath elevator portion 156. Alternatively, the light source can include light emitting diodes provided just below illumination lens 220 to realize additional space savings in the distal section of endoscope 150 and to facilitate modular construction of camera module 162.

Appreciably, referencing FIGS. 6A, 8 and 9, second axis 176 can pass through illumination unit 152 and elevator portion 156. Similarly, first axis 178 can pass through imaging unit 154 and elevator portion 156. First axis 178 and second axis 176 can each be parallel to longitudinal axis 174. Further, referencing FIGS. 6A, 8 and 9, illumination lens optical axis 224 and objective lens optical axis 230 can be parallel to one another. Accordingly, illumination lens optical axis 224 and objective lens optical axis 230 can each be non-parallel to any of first axis 178, second axis 176, and longitudinal axis 174. In examples, illumination lens optical axis 224 and objective lens optical axis 230 can each be generally perpendicular to any of first axis 178, second axis 176, and longitudinal axis 174.

Embodiments of FIGS. 6A, 6B, 8 and 9 can advantageously result in a reduced diameter of the distal section of the endoscope 150 in comparison to the diameter of the distal section of the endoscope 50 illustrated in FIGS. 3 and 4.

Figure 10:
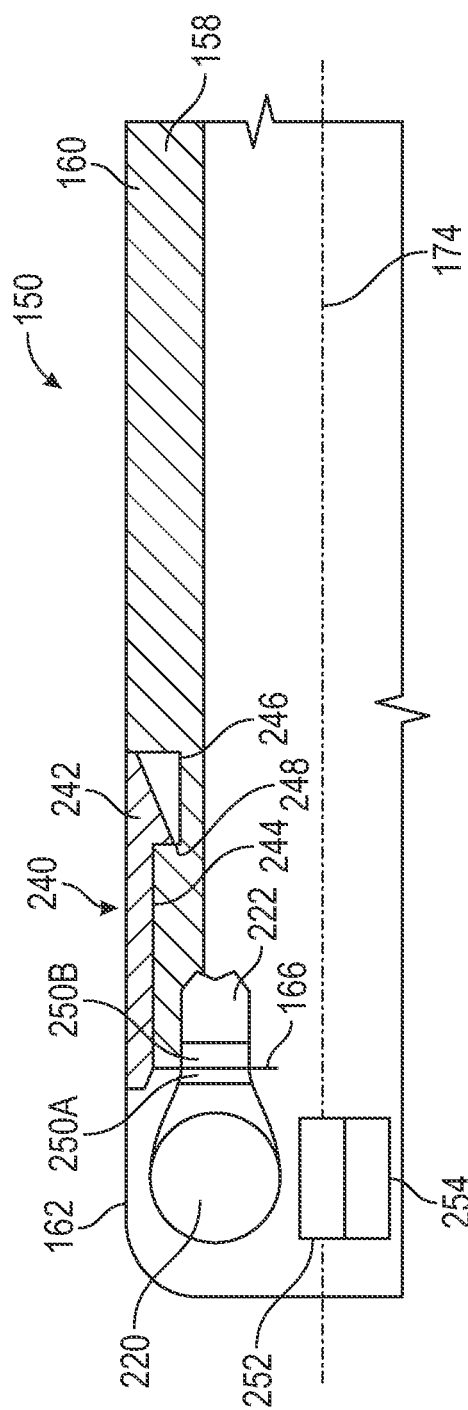
FIG. 10 is a schematic illustration of a distal portion of an endoscope of the present disclosure including an attachment mechanism for detachable camera module.

FIG. 10 illustrates attachment mechanism 240 for connecting camera module 162, including imaging unit 154 and illumination unit 152, to elevator housing 160, according to examples. In the illustrated example, attachment mechanism 240 is shown as coupling imaging unit 154 and illumination unit 152 simultaneously to elevator housing 160 via camera module 162. However, in other examples, imaging unit 154 and illumination unit 152 can be individually coupled to elevator housing 160 by separate attachments mechanisms. Attachment mechanism 240 can be configured to allow for user detachment of camera module 162 from elevator housing 160 (and/or other portions of insertion sheath 158).

Attachment mechanism 240 can comprise a snap engagement feature, provided by locking tab 242. Locking tab 242 can be disposed at an end of stem 244 attached to camera module 162, or illumination unit 154 or imaging unit 152 in other examples. Recess 246 can be provided on an outer surface of elevator housing 160 to form ledge 248. Recess 246 can be sized to receive locking tab 242 and form a secure connection. In examples, locking tab 242 can be configured to be detached by a tool to release locking tab 242 from recess 246 and separate camera module 162, or illumination unit 152 or imaging unit 154, from elevator housing 160. For example, stem 244 can deflect to allow locking tab 242 to slide past recess 246. However, stem 244 can be sufficiently resilient to hold locking tab 242 within recess 246 unless acted upon by an external force, for example. Such embodiments can be suitable in instances where a secure connection between camera module 162 (e.g., the combination of imaging unit 154 and illumination unit 152) and elevator portion 156 is desired during insertion. In other examples, other types of attachment mechanism can be used in lieu of or in conjunction with attachment mechanism 240, such as the use of fasteners with flanges, latches, threaded couplings and the like. Low-profile coupling mechanisms, such as attachment mechanism 240, are advantageous in reducing diameter and reducing friction, which facilitates insertion into the anatomy Endoscope 150 can further comprise couplers 250A and 250B for connecting portions of light conduit 222 at joint line 166 for wired operation of camera module 162. Thus, a portion of light conduit 222 distal of coupler 250A can connect to lens 220 and a portion of light conduit 222 proximal of coupler 250B can connect to light source 22 (FIG. 1). Couplers 25A and 250B can comprise and suitable couplers for joining sections of light conduit 222. In an example, couplers 250A and 250B can comprise magnetic couplers. In other examples, ends of light conduit 222 can be laid end-to-end without couplers. Imaging unit 152 can additionally be provided with couplers similar to couplers 250A and 250B for cable 216. Use of such couplers, can be advantageous for use with self-contained camera modules where photosensitive element 214, wireless communication device 252 and light generator 254 included within camera module 162. The couplers described with reference to FIG. 10 can additionally be used with camera module 162 of FIGS. 8 and 9, as well as wireless communication device 252 and light generator 254.

Prior to insertion of the endoscope 150 according to some embodiments, detachable camera module 162 (including imaging unit 154 and illumination unit 152) can be attached to elevator housing 160 via locking tab 242. Endoscope 150 can be inserted to a target region and images of the target region can be collected. Endoscope 150 can be removed and camera module 162 can be detached from elevator housing 160, e.g., with or without use of a tool. Camera module 162 can be sterilized prior to reuse. Elevator housing 160, including elevator portion 156 therein, and insertion sheath 158 can be disposed after use. Alternatively, elevator housing 160 and elevator portion 156 and insertion sheath 158 can also be sterilized and reused.

Figure 11:
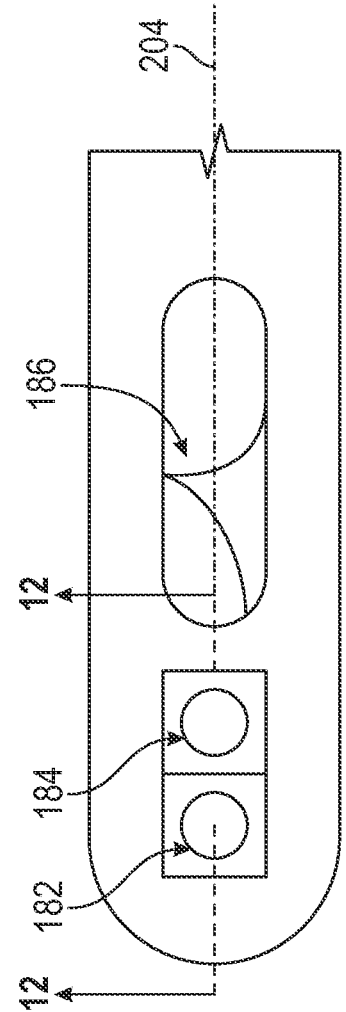
FIG. 11 is a schematic illustration of a distal portion of an endoscope of the present disclosure including a wide-angle lens.
Figure 12:
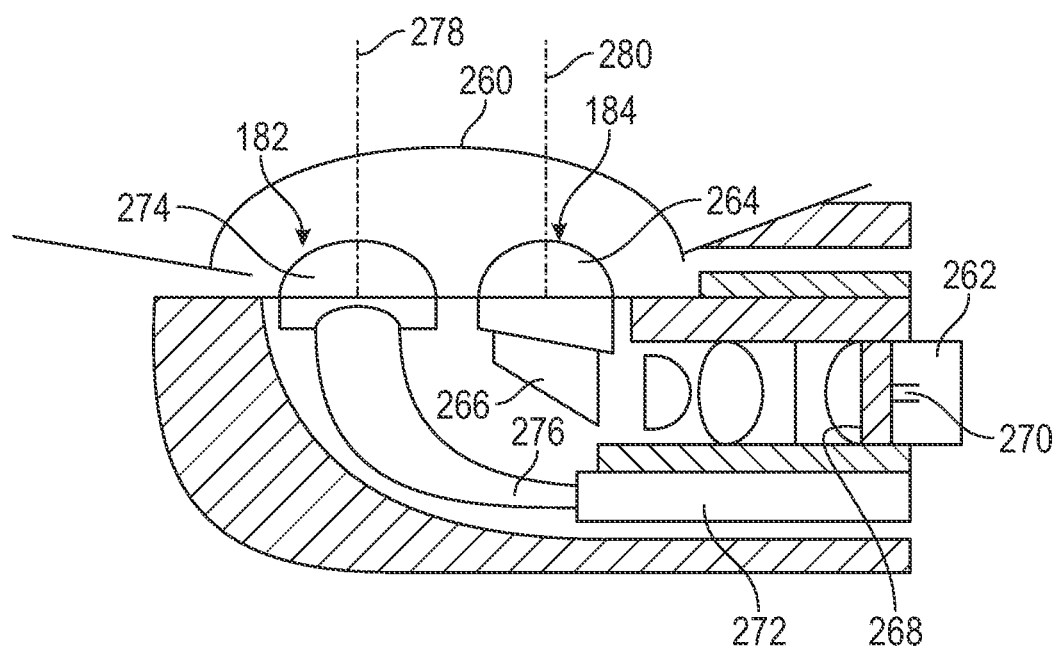
FIG. 12 is a schematic cross-sectional view of the distal portion of the endoscope of FIG. 1 taken at plane 12-12 showing a profile of the wide-angle lens.

FIGS. 11 and 12 illustrate a distal section of endoscope 150 according to another example. FIGS. 11 and 12 are generally similar to the embodiment illustrated in FIG. 7A with the addition of wide-angle lens 260. In the example of FIGS. 11 and 12, longitudinal axis 204 passes through each of elevator portion 186, illumination unit 182 and imaging unit 184. Imaging unit 184 can comprise imaging unit passageway 262, lens 264, prism 266, photosensitive element 268 and cable 270. Illumination unit 182 can comprise illumination unit passageway 272, lens 274 and light conductor 276. Furthermore, illumination lens optical axis 278 and objective lens optical axis 280 can each be generally non-parallel (e.g., perpendicular) to longitudinal axis 204.

In the illustrated example of FIGS. 11 and 12, illumination unit 182 and imaging unit 184 can be configured to permit "wide angle" illumination and/or imaging for side-viewing endoscopes. Wide-angle imaging can permit imaging of a portion of the target anatomy situated directly above the elevator portion. In one embodiment, wide angle illumination and/or imaging can be accomplished by providing illumination lens 274 and/or objective lens 264 with a field of view between about one-hundred-fifty degrees and about one-hundred-eighty degrees (inclusive). In examples, illumination lens 274 and objective lens 264 can each have a field of view of about one-hundred-seventy degrees. In another example, either or both of illumination lens 274 and objective lens 264 can be configured as a "fisheye" type lens. Accordingly, imaging unit 184 and illumination unit 182 can permit wide angle imaging and image areas that are situated above (e.g., directly above) elevator portion 186, such as portions immediately radially outward of elevator portion 186 relative to axis 204.

FIG. 13 is a perspective view of elevator portion 156 of the present disclosure suitable for use with low-profile endoscopes 150 and 180, as well as other endoscopes. Elevator portion 156 can comprise elongate body 300, first end portion 302, second end portion 304, arcuate section 306, guide 308, portal 310 and space 311. Elevator portion 156 can comprise an elevator mechanism for deflecting an instrument extending along axes 174 and 204 within insertion passageways 172 and 202, respectively, as explained with reference to FIGS. 16-19.

Figure 14:
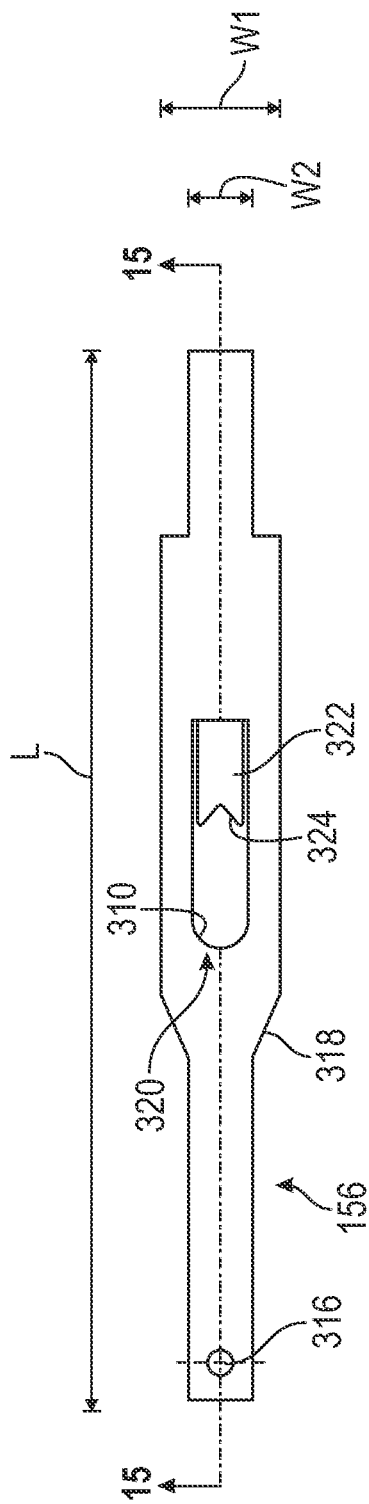
FIG. 14 is a top view of the elevator mechanism of FIG. 13 in a flattened state.
Figure 15:
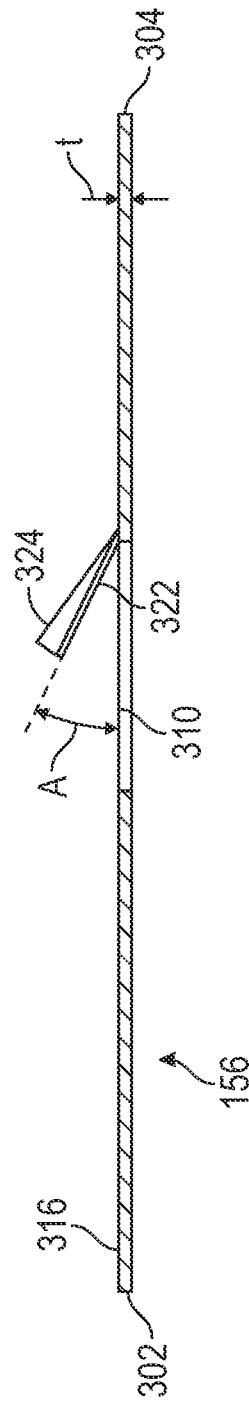
FIG. 15 is a side cross-sectional view of the elevator mechanism of FIG. 13 taken at plane 13-13 showing an instrument guide flange.
Figure 16:
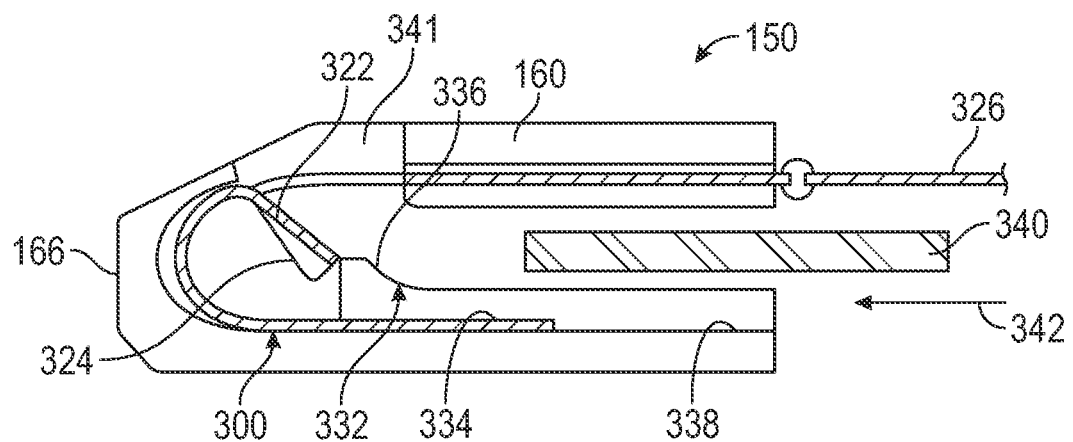
FIG. 16 is schematic cross-sectional view of the elevator mechanism of FIG. 13 showing an instrument located in an insertion passageway retracted from the elevator mechanism.

Elongate body 300 can comprise a unitary, generally planar sheet, as illustrated in FIGS. 14 and 15, shaped into the geometry of FIG. 13. First end portion 302 can be shaped to include retention features, such as flange 312 forming shoulder 314. Second end portion 304 can comprise coupler 316 and planar portion 318. Planar portion 318 can link second end portion 304 with guide portion 320 and can include flared portions necking down width W2 of guide portion 320 down to width W1 of second end portion 304. Guide portion 320 can be selectively widened to accommodate features of the elevator mechanism. Guide portion 320 can comprise guide 308 and portal 310. Guide 308 can include a chute comprise tab or flange 322 and groove or channel 324.

First end portion 302 can be configured to be secured to the distal portion of endoscope 150, such as at sheath 158, or endoscope 180, such as at sheath 188. In examples, flange 312 can be secured to sheath 158 by pinching, crimping or any other suitable method. In additional examples, first end portion 302 can be provided with connectors, such as clamps and the like. As such, elevator portion 156 can be configured to be secured to sheath 158. First end portion 302 can thus be secured to endoscope 150 by a non-rotating or non-hinged connection to fixedly anchor elevator portion 156. In certain examples, the connection of first end portion 302 to sheath 158 can be non-user removable, e.g., elevator portion 156 cannot be removed from sheath 158 without destructive procedures. Accordingly, first end portion 302 can be secured to the distal portion of sheath 158 at the time of manufacture and assembly and cannot be separated thereafter. Fixing of first end portion 302 can facilitate actuation of second end portion 304 to flex arcuate section 306 to activate flange 322.

Second end portion 304 can be configured to connect to an elevator actuation mechanism. In examples, the elevator actuation mechanism can include a pull-wire assembly including pull wire 326 secured to handle 32 (FIGS. 1 and 2). More specifically, pull wire 326 can be coupled to one or more actuators (e.g., knob 38 of FIG. 2), that can be turned by an operator (e.g., using their thumb or fingers), to control tension. Pull wire 326 can be secured to second end portion 304 at coupler 316, such as by tying or welding, etc. Pull wire 326 can transmit the tension to second end portion 304 of elongate body 300, resulting in second end portion 304 being pulled proximally, or pushed distally, along the arrows 328 and 330 shown in FIG. 13, respectfully. The pushing/pulling exerted on second end portion 340 of elevator portion 156 can help orient one or more endotherapy tools supported within space 311 (e.g., at flange 322) by elevator portion 156, as is discussed with reference to FIGS. 16-19. Space 311 can therefor form a guide passage for directing endotherapy instrument 340 (FIG. 16) through elongate body 300 to into opening 310, which can form a guide slot for directing endotherapy instrument 340 out of elongate body 300.

FIG. 14 is a top view of elongate body 300 of FIG. 13 in a flattened state. FIG. 15 is a side cross-sectional view of elongate body 300 of FIG. 13 taken at plane 15-15 showing instrument guide flange 322. FIGS. 14 and 15 are discussed concurrently. The sheet of elongate body 300 can have thickness t substantially less than width W1 or length L. The sheet may be, in some advantageous embodiments, made of stainless steel. Alternatively, other materials (alloys or non-metallic elements) are also contemplated. Elevator portion 156 can be formed from the sheet by a variety of manufacturing techniques to result in the shape shown in FIG. 13. In examples, elevator portion 156 can be formed by precision stamping of the sheet into the shape shown in FIG. 14. In an example, a flat sheet having a rectangular shape can be positioned relative to a stamping machine. A die having the shape of elongate body 300 can be loaded in the stamping machine. The stamping machine can be activated to press the die against the flat sheet to thereby form elongate body 300 shown in FIGS. 14 and 15. In examples, elongate body 300 can be simultaneously stamped to form channel 324 in flange 322. Likewise, elongate body 300 can be simultaneously stamped to bend flange 322 to angle A shown in FIG. 15 and form coupler 316. In other examples, the outline of elongate body 300, flange 322 and portal 310 can be formed by separate stamping steps, and the shape of channel 324, the angle of flange 322 and coupler 316 can be formed by one or more subsequent steps.

FIGS. 16-19 illustrate sectional views of elevator portion 156 positioned in a distal section of side-viewing endoscope 150 according to any of the disclosed embodiments. Although described with reference to endoscope 150, operation of elevator portion 156 can function similarly with endoscope 180. FIGS. 16-19 can be particularly suitable when the side-viewing scope has an "in-line" arrangement of the elevator portion and the camera module (e.g., such as the embodiments of FIGS. 6A and 7A, described further in U.S. 62/958,041 filed on Jan. 7, 2020, tided, "Endoscope with a Low-Profile Distal Section," the entire contents of which are hereby incorporated by reference. Accordingly, the embodiments of FIGS. 16-19 can include more space further distally of elevator portion 156 to house camera module 160. Thus, the distal tip of elevator housing 162 shown in FIGS. 16-19 can comprise joint line 166.

With reference to FIGS. 16-19, the distal section of endoscope 150 can, in some examples, include ramp 332. Ramp 332 can include first surface 334, and second surface 336 opposite to first surface 334. First surface 334 of ramp 332 can abut first end portion 302 of elongate body 300. First end portion 302 can be sandwiched between first surface 334 of ramp 332 and interior surfaces of the distal section of endoscope 150 during assembly. In some examples, first end portion 302 can be fixed with respect to first surface 334 of ramp 332, or with respect to interior surfaces of the distal section of endoscope 150. In addition, the assembly process can secure first end portion 302 and first surface 334 of ramp 332 to the interior surfaces of elongate body 300 so that no gaps or other areas are present between first end portion 302, first surface 334 of ramp 332 and the interior surfaces of elevator portion 156, to reduce or avoid ingress of biological matter. Second surface 336 of ramp 332 can be generally suitable for providing initial guidance of endotherapy instrument 340 (e.g., guidewire, catheter, or secondary scope) as such instrument approaches the distal section in instrument lumen 338. Second surface 336 can therefore be oriented so as to be non-parallel to first surface 334 of ramp 332. Elevator portion 156 can be positioned such that flange 322 extends in the space available in the distal section of endoscope 150, and flange 322 is close to or in abutment with second surface 336 of ramp 332.

Figure 17:
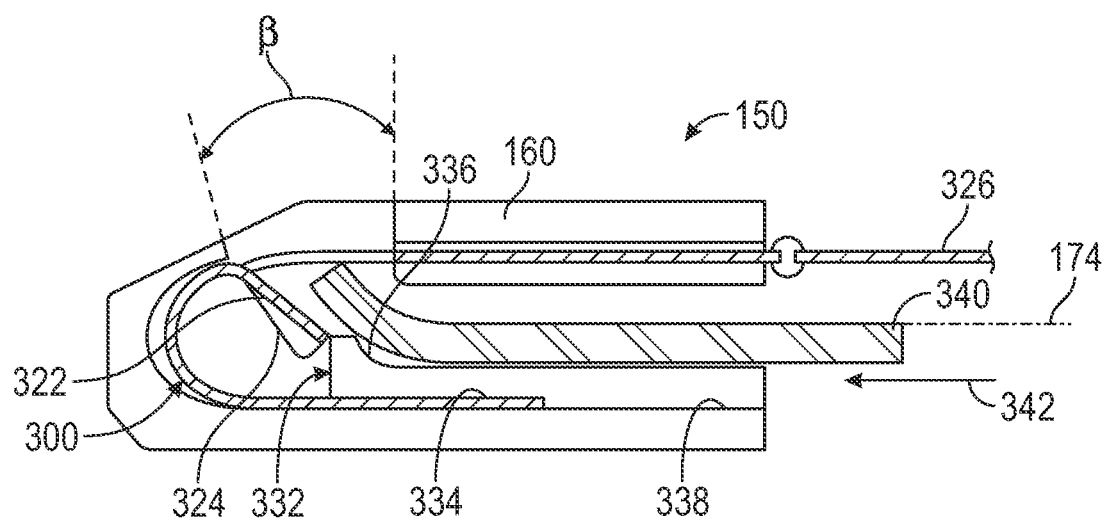
FIG. 17 is schematic cross-sectional view of the elevator mechanism of FIG. 14 showing the instrument advanced through the insertion passageway to engage a guide flange of the elevator mechanism.

With reference to FIG. 17, flexible arcuate section 306 of elevator portion 156 (which extends between first end portion 302 and flange 322) can at least partially be movable with respect to first end 302 and ramp 332, when second end 304 of elevator portion 156 is actuated (e.g., by pull wire 326). At least portions of arcuate section 306 of elevator portion 156 cannot directly abut or directly connect to any other portion of the distal section of elevator portion 156, and can move in the space surrounding arcuate section 306. Ramp 332 can be positioned proximate opening 341 on elevator housing 160. Elevator housing 160 can further comprise pocket 169 for storing arcuate section 306 in an un-deflected state. Opening 341 can be configured to receive endotherapy instrument 340 from ramp 332. As can be seen in FIG. 17, second surface 336, flange 322 and opening 341 can form exit angle β relative to perpendicular of longitudinal axis 174. Thus, endotherapy instrument 340 can be pushed to engage second surface 336, which can turn the distal end of endotherapy instrument 340 toward flange 322 and initially orient the distal end of endotherapy instrument 340 at angle β.

Figure 18:
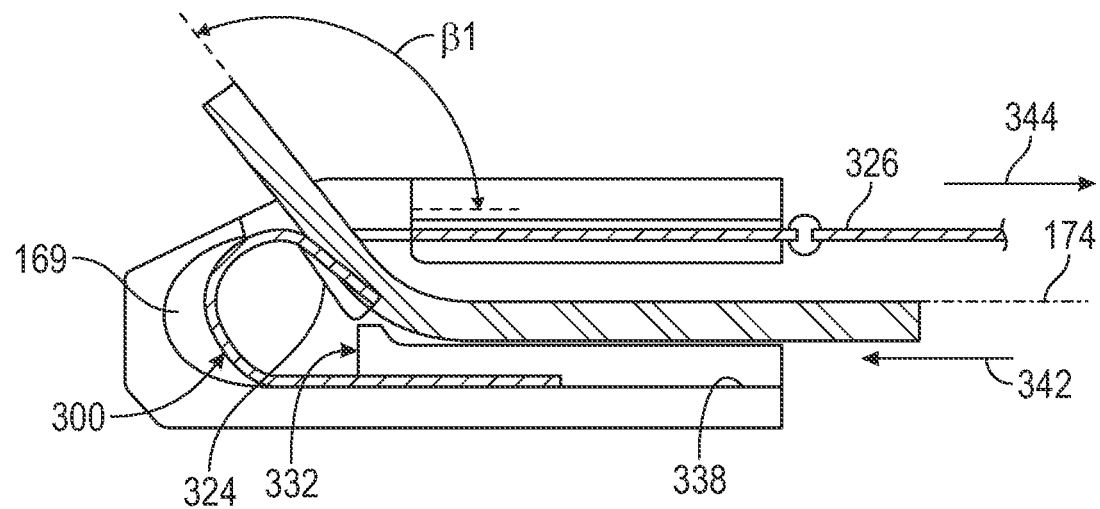
FIG. 18 is schematic cross-sectional view of the elevator mechanism of FIG. 17 showing the instrument advanced through the elevator mechanism to protrude from the endoscope at a first angle.

With reference to FIG. 18, endotherapy instrument 340 can be further advanced in the direction of arrow 342 until the distal end of endotherapy instrument 340 protrudes through opening 341. Endotherapy instrument 340 can protrude from opening 341 at angle β1 with reference to longitudinal axis 147. Angle β1 can be equal to angle β plus ninety-degrees.

Figure 19:
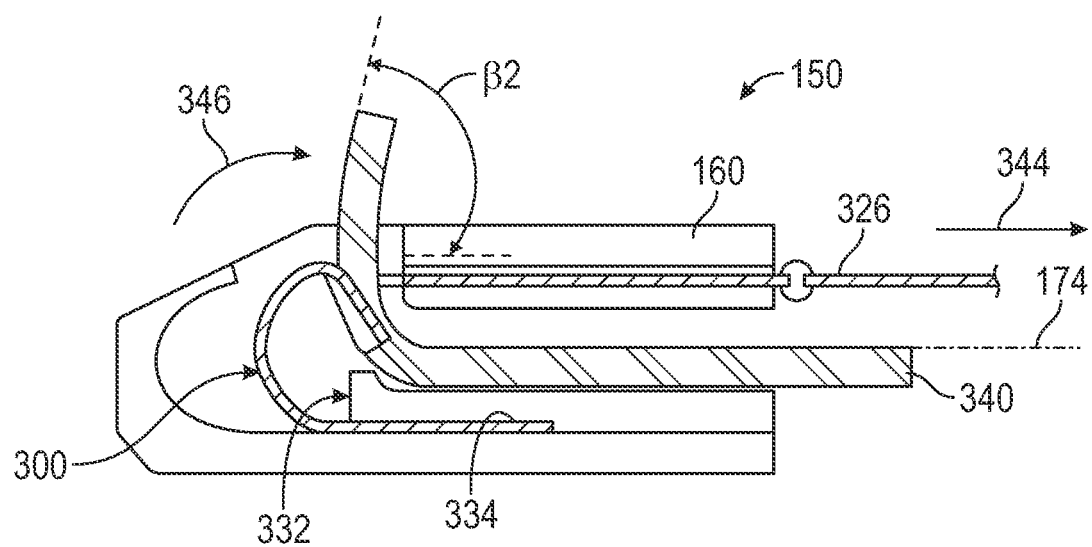
FIG. 19 is schematic cross-sectional view of the elevator mechanism of FIG. 18 showing the elevator mechanism being activated to bend the instrument with the guide flange to a second angle.
Figure 20:
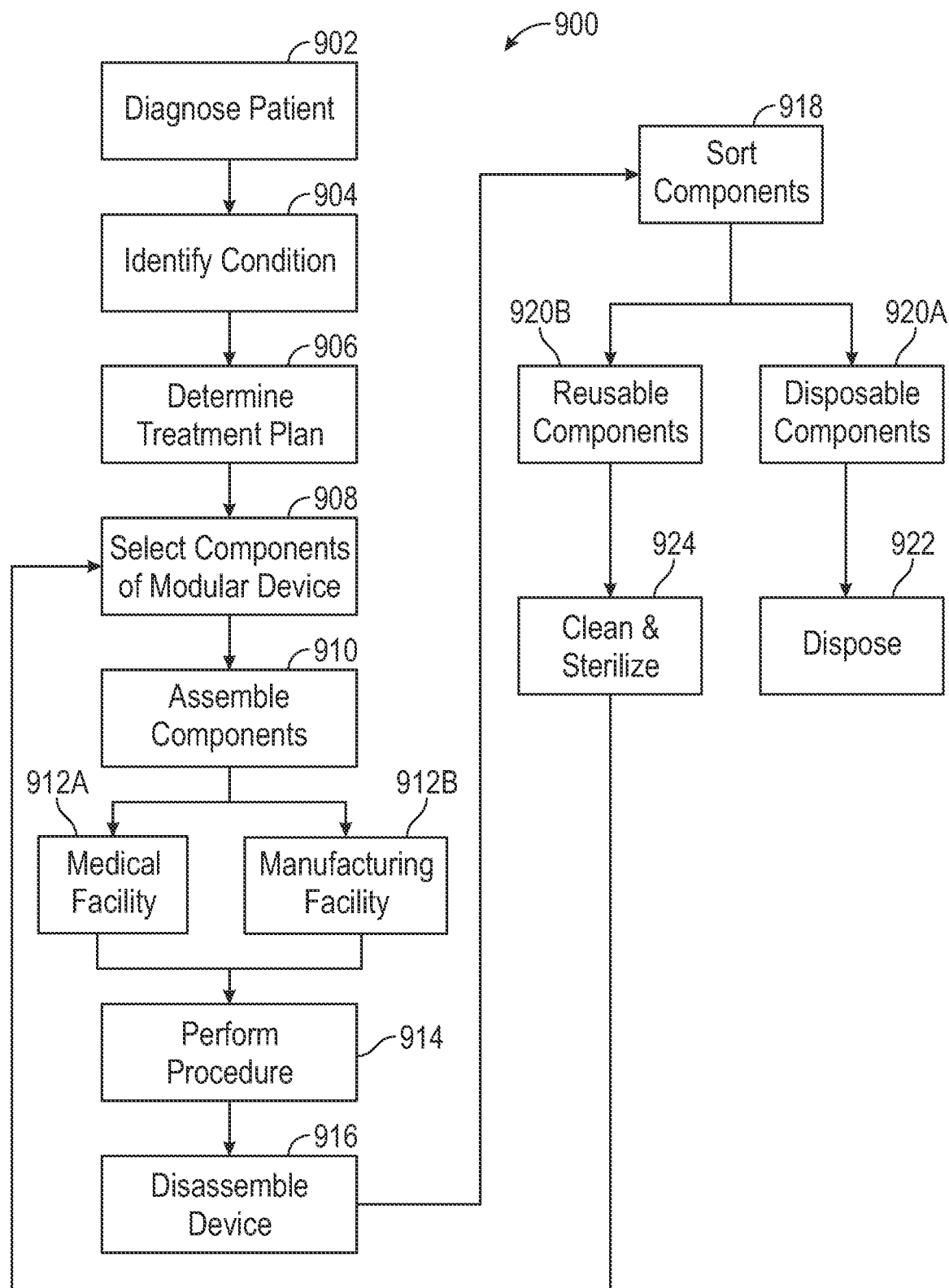
FIG. 20 is a block diagram illustrating a method of processing modular endoscope components for performing a surgical procedure.

With reference to FIG. 19, elevator portion 156 can be actuated further to provide additional guiding and orientation of endotherapy instrument 340. For instance, elevator portion 156 can be actuated by pulling, e.g., via knobs 38 on endoscope handle 32 (FIG. 2), which exerts a force on second end portion 304 of elevator portion 156 in direction shown by arrow 344 opposite to the direction of advancement arrow 342 of endotherapy instrument 340. As second end portion 304 of elevator portion 156 is actuated, arcuate portion 306 can rotate along the direction indicated by arrow 346 relative to first end portion 302, and advance the guiding portion toward instrument 340. In certain advantageous aspects, the pulling force exerted on second end portion 304 of elevator portion 156 can additionally move channel 324 proximally in the direction of arrow 344 to catch on to instrument 340, and thereby self-seat instrument 340 in channel 324. Once seated, no relative motion between channel 324, flange 322 and instrument 340 can be permitted. Further actuation of elevator portion 156 (e.g., by pulling further on second end portion 304 of elevator portion 156) can move flange 322 and instrument 340 seated in channel 324 in sync and adjust the angle of instrument 340 relative to first surface 334 of ramp 332, and without moving or unseating instrument 340 from channel 324. Elevator portion 156 can be actuated to position the distal end of endotherapy instrument 340 at angle β2 relative to longitudinal axis 174.

Embodiments such as those of FIGS. 16-19 can be suitable for use with endoscopes that are single-use or reusable. Examples such as those described herein can also be suitable for use with endoscopes that are reusable. Unlike conventional endoscope mechanisms, elevator portion 156 according to the examples illustrated herein can be easier to clean due to the absence of several small interconnected pieces unlike conventionally available elevator mechanisms. Accordingly, the disclosed elevator mechanisms of the present disclosure can improve procedure and patient safety by reducing ingress of biological material (e.g., antibiotic resistant bacteria) between uses and/or patients. The single-piece construction of the elevator can reduce cost of manufacture.

FIG. 23 is a block diagram illustrating method 900 of processing modular endoscope components for performing a surgical procedure. At step 902, a specific patient can be diagnosed as having a particular condition or as needing a particular evaluation. A surgeon or other qualified medical professional can perform the diagnosis.

At step 904, a particular condition of the patient can be identified as needing interaction from a particular therapy or evaluative procedure. For example, a particular organ or anatomic region can be identified as needing a specific intervention or evaluation.

At step 906, a particular treatment plan can be developed to address the condition identified at step 904. The treatment plan can include selection of a therapy to be performed, such as ablation, freezing, cauterizing, cutting, attaching and the like. The treatment plan can also include a plan for performing a surgical technique, such as instructions for delivering the selected therapy to the particular organ or anatomic regions, such as by using a camera-enabled endoscope.

At step 908, components of a medical device to deliver the selected therapy can be selected. For example, a particular treatment module can be selected to provide the selected therapy, a particular sheath or shaft can be selected to deliver the treatment module, and a particular control module can be selected to control operation of the modular medical device. Features and characteristics of the selected sheath or shaft can be selected, such as the number of delivery lumens needed to provide the treatment, guidance and steering capabilities needed for the selected treatment plan and therapy. Likewise, a camera module can be selected to facilitate guiding of the treatment module and viewing of the anatomic region or organ.

At step 910, the selected components of step 908 can be assembled. The selected components can be assembled at a medical facility where the procedure is to be performed, at step 912A. For example, the modular components can be user-assembled. In particular, a camera module can be attached using an attachment mechanism, such as a deflectable tab. The selected components can be assembled at a manufacturing facility, at step 912B.

At step 914, the procedure planned for at step 906 can be performed with the medical device assembled at step 910.

At step 916, the assembled medical device used in the procedure at step 914 can be disassembled. The medical device can be disassembled at the medical facility of step 912A or can be sent offsite to be disassembled at the manufacturing facility of step 912B or another repurposing facility. The modular components can be user-disassembled by operating an attachment mechanism.

At step 918, the disassembled components can be sorted into components that can be disposed of at step 920A and components that can be reused at step 920B.

At step 922, the disposable components can be disposed of, such as by being destroyed or discarded. The disposable components can comprise a disposable insertion sheath.

At step 924, the reusable components of step 920B can be cleaned and sterilized for reuse. The reusable components can comprise a detachable camera module. As such, the cleaned and sterilized components can be returned to inventory of the medical facility or manufacturing facility to be used in additional procedures.

Various Notes and Examples

Example 1 can include or use subject matter such as an elevator for a side-viewing endoscope that can comprise a first end secured to an interior surface of a distal portion of the side-viewing endoscope, a second end generally opposite to the first end, the second end being movable with respect to the first end by an actuator of the side-viewing endoscope, a flexible portion positioned between the first end and the second end, the flexible portion rotatable with respect to the first end when the second end is moved by the actuator, and a guide portion extending between the flexible portion and the second end to receive an endotherapy instrument extending from an instrument channel of the side-viewing endoscope, the guide portion comprising a chute configured to guide a distal end of the endotherapy instrument as the distal end leaves the distal portion of the side-viewing endoscope.

Example 2 can include, or can optionally be combined with the subject matter of Example 1, to optionally include each of the first end, the second end, the flexible portion and the guide portion being co-extensive with one another.

Example 3 can include, or can optionally be combined with the subject matter of one or any combination of Examples 1 or 2 to optionally include the flexible portion being shaped such that portions of the elongate body extending from the first and second ends oppose each other to form a guide passage.

Example 4 can include, or can optionally be combined with the subject matter of one or any combination of Examples 1 through 3 to optionally include an elevator further comprising a first planar portion extending between the guide portion and the second end.

Example 5 can include, or can optionally be combined with the subject matter of one or any combination of Examples 1 through 4 to optionally include an elevator that further comprises a second planar portion extending between the flexible portion and the first end, wherein the second planar portion is parallel to the first planar portion.

Example 6 can include, or can optionally be combined with the subject matter of one or any combination of Examples 1 through 5 to optionally include a flexible portion that is non-parallel to the first planar portion.

Example 7 can include, or can optionally be combined with the subject matter of one or any combination of Examples 1 through 6 to optionally include a guide portion that includes a guide surface extending from the guide portion non-parallel to the first planar portion.

Example 8 can include, or can optionally be combined with the subject matter of one or any combination of Examples 1 through 7 to optionally include a guide surface that comprises an instrument retainer configured to non-movably couple an endotherapy instrument to the guide surface.

Example 9 can include, or can optionally be combined with the subject matter of one or any combination of Examples 1 through 8 to optionally include a guide portion that includes a guide slot generally surrounding the guide surface.

Example 10 can include or use subject matter such as an endoscope that can comprise an insertion sheath defining a lumen, and an elongate body defining an elevator positioned at least partially within the lumen, the elongate body comprising a first end portion for anchoring to an internal passage of the endoscope, a second end portion for coupling to an actuator of the endoscope, an arcuate section positioned between the first and second end portions, the arcuate section being curved to define an interior space between opposing sections of the elongate body, a guide extending from the elongate body into the interior space, and a portal extending through the elongate body adjacent the guide.

Example 11 can include, or can optionally be combined with the subject matter of Example 10, to optionally include an elevator that extends along an axis from a proximal end proximate the first and second end portions to a distal end proximate the arcuate section.

Example 12 can include, or can optionally be combined with the subject matter of one or any combination of Examples 10 or 11 to optionally include a guide that comprises a deflectable tab angled inward from the portal in a proximal direction.

Example 13 can include, or can optionally be combined with the subject matter of one or any combination of Examples 10 through 12 to optionally include a guide that further comprises a catch groove extending along a path that intersects the axis.

Example 14 can include, or can optionally be combined with the subject matter of one or any combination of Examples 10 through 13 to optionally include opposing sections of the elongate body that comprise a first section connected to the first end portion and a second section connected to the second end portion.

Example 15 can include, or can optionally be combined with the subject matter of one or any combination of Examples 10 through 14 to optionally include an arcuate section that comprises a u-shaped body connecting the first section and the second section.

Example 16 can include, or can optionally be combined with the subject matter of one or any combination of Examples 10 through 15 to optionally include a coupler for linking the second end portion of the elongate body to an actuator.

Example 17 can include, or can optionally be combined with the subject matter of one or any combination of Examples 10 through 16 to optionally include a first end portion that comprises a flange extending axially from a shoulder to define an end of the first end portion.

Example 18 can include, or can optionally be combined with the subject matter of one or any combination of Examples 10 through 17 to optionally include a ramp disposed within the interior space having a curved surface positioned to align with the guide, and an opening in the lumen.

Example 19 can include or use subject matter such as a method of forming an elevator for an endoscope that can comprise forming from a planar sheet of material an elongate body comprising a length between a first end and a second end, a width less than the length, and a thickness less than the length and width, forming a guide body in the elongate body, bending the elongate body such that first and second lengths of the elongate body oppose each other to form an interior space, and bending the guide body to extend into the interior space.

Example 20 can include, or can optionally be combined with the subject matter of Example 19, to optionally include forming the elongate body and forming the guide body as a single process.

Example 21 can include, or can optionally be combined with the subject matter of one or any combination of Examples 19 or 20 to optionally include the single process comprising a stamping process or an etching process.

Example 22 can include, or can optionally be combined with the subject matter of one or any combination of Examples 19 through 21 to optionally include a the single process further forming an actuator coupling proximate the first end, and a retention feature proximate the second end.

Example 23 can include, or can optionally be combined with the subject matter of one or any combination of Examples 19 through 22 to optionally include forming a guide groove in the guide body.

Example 24 can include, or can optionally be combined with the subject matter of one or any combination of Examples 19 through 23 to optionally include forming the guide slot by bending the guide body to form a channel therein.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An elevator for a side-viewing endoscope, comprising:
   a first end secured to an interior surface of a distal portion of the side-viewing endoscope;
   a second end generally opposite to the first end, the second end being movable with respect to the first end by an actuator of the side-viewing endoscope;
   a flexible portion positioned between the first and the second end, the flexible portion rotatable with respect to the first end when the second end is moved by the actuator from an un-deflected position to an actuated position, wherein the flexible portion is curved such that the second end portion is opposed and parallel to the first end portion in both the un-deflected portion and the actuated position; and
   a guide portion extending between the flexible portion and the second end to receive an endotherapy instrument extending from an instrument channel of the side-viewing endoscope, the guide portion comprising a chute configured to guide a distal end of the endotherapy instrument as the distal end leaves the distal portion of the side-viewing endoscope.

2. The elevator of claim 1, wherein, each of the first end, the second end, the flexible portion and the guide portion extend contiguously along an axial path.

3. The elevator of claim 2, wherein the flexible portion is shaped such that portions of the elevator extending from the first and second ends oppose each other to form an internal guide passage in the actuated position and the un-deflected position.

4. The elevator of claim 1, wherein the elevator further comprises a first planar portion extending between the guide portion and the second end.

5. The elevator of claim 4, wherein the elevator further comprises a second planar portion extending between the flexible portion and the first end, wherein the second planar portion is parallel to the first planar portion, wherein the first planar portion, the second planar portion and the flexible portion are formed of a continuous sheet metal body having uniform thickness.

6. The elevator of claim 5, wherein the guide portion includes a guide surface extending from the guide portion non-parallel to the first planar portion, wherein the guide surface is configured to guide an instrument through the elevator in a direction extending in a direction transverse to the first planar portion and the second planar portion.

7. The elevator of claim 6, wherein the guide surface comprises an instrument retainer configured to non-movably couple an endotherapy instrument to the guide surface.

8. The elevator of claim 6, wherein the guide portion includes a guide slot generally surrounding the guide surface.

9. The elevator of claim 4, wherein the flexible portion is non-parallel to the first planar portion.

10. An endoscope comprising:
an insertion sheath defining a lumen; and
an elongate body defining an elevator positioned at least partially within the lumen, the elongate body comprising:
  a first end portion for anchoring to an internal passage of the endoscope;
  a second end portion for coupling to an actuator of the endoscope;
  an arcuate section positioned between the first and second end portions, the arcuate section being curved to define an interior space between opposing sections of the elongate body;
  a first side extending along the first end portion, arcuate section and second end portion to define an interior surface bordering the interior space;
  a second side extending along the first end portion, arcuate section and second end portion opposite the first side to face toward the lumen;
  a guide extending from the elongate body into the interior space; and
  a portal extending through the elongate body adjacent the guide to allow passage of an instrument from within the interior space through the first and second sides of the elongate body.

11. The endoscope of claim 10, wherein the elevator extends along an axis from a proximal end proximate the first and second end portions to a distal end proximate the arcuate section.

12. The endoscope of claim 11, wherein the guide comprises a deflectable tab angled inward from the portal in a proximal direction.

13. The endoscope of claim 12, wherein the guide further comprises a catch groove extending along a path that intersects the axis.

14. The endoscope of claim 10, wherein the opposing sections of the elongate body comprise a first section connected to the first end portion and a second section connected to the second end portion.

15. The endoscope of claim 14, wherein the arcuate section comprises a u-shaped body connecting the first section and the second section such that the second end portion is proximal of the first end portion.

16. The endoscope of claim 10, further comprising a coupler for linking the second end portion of the elongate body to the actuator.

17. The endoscope of claim 10, wherein the first end portion comprises a flange extending axially from a shoulder to define an end of the first end portion.

18. The endoscope of claim 10, further comprising:
a ramp disposed within the interior space having a curved surface positioned to align with the guide, the ramp comprising a stationary component mounted within the endoscope separate from the elevator to guide an instrument onto the guide; and
an opening in the lumen aligned with the ramp and the guide.

19. A method of forming an elevator for an endoscope, the method comprising:
forming from a planar sheet of material an elongate body comprising:
  a length between a first end and a second end;
  a width less than the length; and
  a thickness less than the length and width;
forming a guide body in the elongate body;
bending the elongate body such that first and second lengths of the elongate body oppose each other to form an interior space; and
bending the guide body to extend into the interior space;
attaching the first end to a shaft of the endoscope; and
attaching the second end to an actuation wire for the endoscope.

20. The method of claim 19, wherein forming the elongate body and forming the guide body comprise a single process.

21. The method of claim 20, wherein the single process comprises a stamping process or an etching process.

22. The method of claim 20, wherein the single process further forms:
an actuator coupling proximate the first end; and
a retention feature proximate the second end.

23. The method of claim 19, further comprising forming a guide groove in the guide body.

24. The method of claim 23, wherein forming the guide groove comprises bending the guide body to form a channel therein.

* * * * *